(12) United States Patent
Danila et al.

(10) Patent No.: US 10,113,200 B2
(45) Date of Patent: Oct. 30, 2018

(54) GENES ASSOCIATED WITH DASATINIB SENSITIVITY

(71) Applicant: MEMORIAL SLOAN-KETTERING CANCER CENTER, New York, NY (US)

(72) Inventors: Daniel C. Danila, New York, NY (US); Howard I. Scher, Tenafly, NJ (US); Martin Fleisher, Glen Cove, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 597 days.

(21) Appl. No.: 14/428,248

(22) PCT Filed: Sep. 16, 2013

(86) PCT No.: PCT/US2013/059958
§ 371 (c)(1),
(2) Date: Mar. 13, 2015

(87) PCT Pub. No.: WO2014/043628
PCT Pub. Date: Mar. 20, 2014

(65) Prior Publication Data
US 2015/0240314 A1    Aug. 27, 2015

Related U.S. Application Data

(60) Provisional application No. 61/701,389, filed on Sep. 14, 2012.

(51) Int. Cl.
*C12Q 1/6886* (2018.01)
*A61K 31/506* (2006.01)
*G06F 19/20* (2011.01)
*G06F 19/00* (2018.01)

(52) U.S. Cl.
CPC .......... *C12Q 1/6886* (2013.01); *A61K 31/506* (2013.01); *G06F 19/20* (2013.01); *G06F 19/3456* (2013.01); *C12Q 2600/106* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2007/0105105 A1    5/2007  Clelland et al.
2010/0120788 A1    5/2010  Wang et al.
2010/0130527 A1    5/2010  Lehrer et al.
2011/0166154 A1    7/2011  Slamon et al.
2011/0183866 A1    7/2011  Clarke et al.

FOREIGN PATENT DOCUMENTS

EP          2405022 A2     1/2012
WO       2010020619 A2     2/2010

OTHER PUBLICATIONS

Wang, et al; "Identification of candidate predictive and surrogate molecular markers for dasatinib in prostate cancer: rationale for patient selection and efficacy monitoring," Genome Biol., 2007, 8(11), pp. R255.1-R255.11.

Mitsiades, et al; "A gene expression signature associated with sensitivity to the multikinase inhibitor dasatinib: Implications for development of a noninvasive biomarker for personalized therapy based on circulating tumor cell anaylsis," 2010 ASCO Annual Meeting Proceedings, Journal of Clinical Oncology, May 20, 2010, vol. 28, No. 15.

Jilaveanu, et al, "In vitro studies of dasatinib, its targets and predictors of sensitivity," Pigment Cell Melanoma Res., Apr. 2011, vol. 24, No. 2, pp. 386-389.

Sanoudou, et al, "Array-based pharmacogenics of molecular-targeted thereapies in oncology," The Pharmacogenomics Journal, Jan. 17, 2012, 12(3), pp. 185-196.

Semenas, et al, "Overcoming drug resistance and treating advance prostate cancer," Curr Drug Targets, Sep. 1, 2012, 13(10), pp. 1308-1323.

Huang, et al, "Identification of candidate molecular markers predicting sensitivity in solid tumors to dasatinib: rationale for patient selection," Cancer Res., 2007, 67(5), pp. 2226-2238.

Moulder, et al; Development of candidate genomic markers to select breast cancer patients for dasatinib therapy, Mol Cancer Ther, 2010, 9(5), pp. 1120-1127.

*Primary Examiner* — Joseph Woitach
(74) *Attorney, Agent, or Firm* — Heslin Rothenberg Farley and Mesiti, PC; Kathy Smith Dias

(57) ABSTRACT

The invention relates to a method for the Cell Type specific labeling with Amino acid Precursors (CTAP). In particular, the disclosed method permits the incorporation of stable isotope-labeled amino acids into the proteome of a vertebrate cell that has been engineered to express an exogenous enzyme that enables the cell to produce an essential amino acid from its amino acid substrate. The method employs stable isotope-labeled amino acid substrate/precursors from which essential amino acids bearing the label are generated. The labeled amino acids generated by the transgenic cell not only supports growth but specifically labels proteins of the transgenic cell. Furthermore, the use of different populations of cells expressing different exogenous amino acid-producing enzymes permits differential labeling of the proteomes of the individual cell populations in multicellular environments.

11 Claims, 23 Drawing Sheets

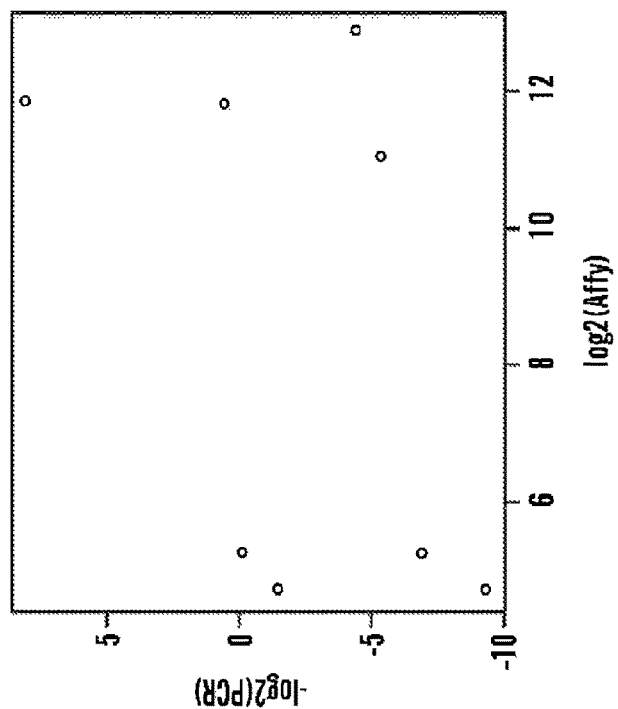
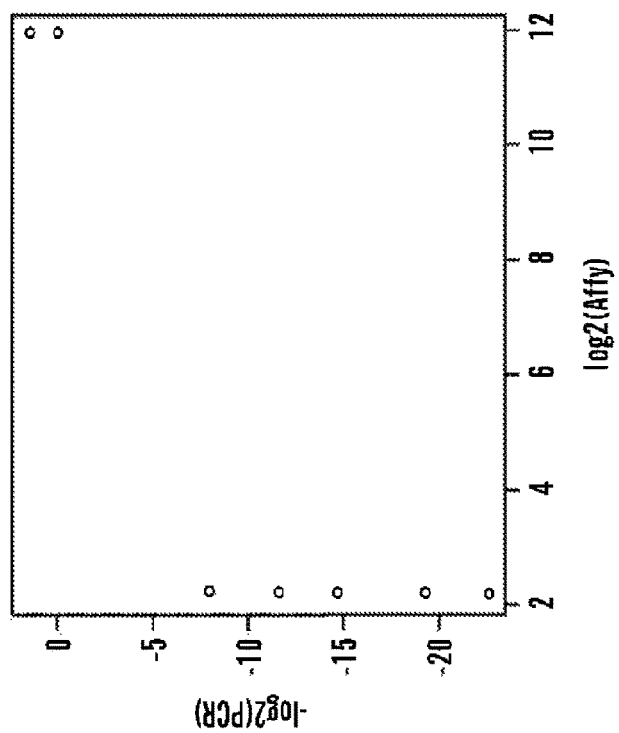
FIG. 5C
FIG. 5D

| CELL LINE | GENES | DASATINIB IC50 |
|---|---|---|
| PC3 | TACTD2, SFN, KRT7, S100A2, COL3A1 | SENSITIVE |
| VCaP | TSPAN8, SPOCK1 | RESISTANT |
| | EXPRESSION PROFILE IN LNCaP PREDICTS A RESISTANT LINE | SENSITIVE |

*FIG. 12*

| CELL LINE | EXPRESSION PROFILE (AFFY SCORE) | RT-PCR PROFILE PROFILE (FLUIDIGM SCORE) |
|---|---|---|
| VCaP | R | -122 (R) |
| LnCaP | R | -92 (R) |
| PC3 | S | 168 (S) |
| MDA | R | -82 (R) |
| 22RV1 | R | -14 (R) |

Score = ((0.114*2^-(TACSTD2/GAPDH))-(0.703*2^-(TSPAN8/GAPDH))-(0.036*2^-(COL3A1/GAPDH))-(0.002*2^-(SPOCK1/GAPDH))+(0.022*2^-(SFN/GAPDH))+(0.514*2^-(KRT17/GAPDH))+(0.518*2^-(S100A2/GAPDH)) x 1,000

FIG. 13 (cont.)

| CRPC PATIENT | RT-PCR SCORE | DASATINIB SIGNATURE PREDICTION |
|---|---|---|
| # 04 | -226 | R |
| # 05 | -204 | R |
| # 11 | 8 | S |
| # 13 | 241 | S |

Score = {(0.114*2^-(TACSTD2/GAPDH))-(0.703*2^-(TSPAN8/GAPDH))-(0.036*2^-(COL3A1/GAPDH))-(0.002*2^-(SPOCK1/GAPDH))+(0.022*2^-(SFN/GAPDH))+(0.514*2^-(KRT17/GAPDH))+(0.518*2^-(S100A2/GAPDH))} × 1,000

*FIG. 15 (cont.)*

GENES ASSOCIATED WITH DASATINIB SENSITIVITY

CROSS-REFERENCE TO RELATED APPLICATIONS

This application is the U.S. National Filing of PCT Application No. PCT/US2013/059958 filed on Sep. 16, 2013 and published in English as WO 2014/043628 A1 on Mar. 20, 2014, and claims the priority of U.S. provisional application Ser. No. 61/701,389 filed Sep. 14, 2012; the contents of each are incorporated by reference in their entirety into the present disclosure.

GOVERNMENT RIGHTS STATEMENT

This invention was made with government support under grant number CA092629 awarded by the National Institutes of Health. The government has certain rights in the invention.

FIELD OF THE INVENTION

The present invention generally relates to prostate cancer and in particular to targeted therapy for prostate cancer patients based on a prospective assessment of the sensitivity of circulating tumor cells obtained from the patient to a therapeutic agent.

BACKGROUND OF THE INVENTION

Prostate cancer is the second leading cause of cancer death in American men, behind only lung cancer. In 2012, it is estimated that about 241,740 new cases of prostate cancer will be diagnosed and about 28,170 men will die of prostate cancer. Treatment options currently available for prostate cancer patients include surgery, radiation, hormonal therapy and chemotherapy. In addition, patients with castration-resistant prostate cancer with bone metastases are often treated with bisphosphonates to prevent skeletal-related events.

As a bone dominant disease, changes in prostate cancer metastases are difficult to assess using conventional imaging modalities,[1,2] and only part of the treatment effect is reflected in serum prostate specific antigen (PSA) changes.[3] Src and other Src family kinases (SFKs) are involved in activating survival, invasion and migration pathways in prostate cancer and may contribute to the initial transition from a castration-sensitive to castration-resistant state by activating the androgen receptor (AR) in an androgen-independent manner (5-14). The expression and activity of the Src kinase is high in osteoclasts and has been reported to be crucial for osteoclast maturation and bone resorptive activity (5, 15-17). SFK activity is increased in castrate resistant prostate cancer (CRPC) and predicts for shorter overall survival (18). Inhibition of Src signaling decreased proliferation, invasion and migration of prostate cancer cell lines in vitro. There is also evidence for direct interaction of Src with steroid receptors in a steroid ligand-independent manner (5). Other dasatinib-sensitive kinases have been implicated in the pathogenesis of metastatic prostate cancer as well; these include EphA2 (19, 20), Lyn (21), PDGFR (22, 23) and c-fms, a key regulator of osteoclastogenesis (24).

Dasatinib is an oral tyrosine kinase inhibitor that inhibits BCR-ABL, Abl, Src and other Src-family kinases (Lck, Hck, Yes, Fgr, Lyn and Fyn), EphA2, c-KIT, PDGFR-α and -β, and the macrophage colony-stimulating factor (M-CSF) receptor, c-fms. Dasatinib is currently approved for the treatment of patients with imatinib-resistant or -intolerant chronic myelogenous leukemia (CML) or Ph+ acute lymphoblastic leukemia (ALL) (1). A Phase III dose optimization study showed that in patients with chronic phase CML, 100 mg once-daily dasatinib improves the safety profile, particularly decreasing pleural effusion and thrombocytopenia, while maintaining efficacy compared with the previously recommended dose of 70 mg twice-daily (1-4).

Evidence from preclinical models of prostate cancer suggests that dasatinib has anti-proliferative and anti-osteoclastic activity and supports the potential of dasatinib as a targeted therapy for prostate cancer (5). Dasatinib also inhibits cell adhesion, migration and invasion in in vitro model systems of prostate carcinoma (25). In orthotopic nude mouse models, dasatinib treatment effectively inhibited both tumor growth and development of lymph node metastases in both castration-sensitive and castration-resistant tumors.

A recent phase II clinical study (Yu et al.) showed dasatinib to be a promising agent for addressing bone morbidity as well as metastasis in chemotherapy-naïve patients with metastatic CRPC, paving the way for a phase III trial evaluating the effects of the addition of dasatinib to docetaxel on overall survival and skeletal-related events.

Prostate cancer is a heterogeneous disease consisting of various forms that differ in their risk of recurrence and response to therapy; the likelihood of treatment success of prostate cancer depends on accurate assessment of disease subtype. Therefore, the need exists for inexpensive and accurate diagnostic methods.

The need for molecular biomarkers from a sample obtained repeatedly and with little inconvenience to the patient and capable of predicting overall survival and responsiveness to treatment has recently focused on the technological advances in circulating tumor cell (CTC) detection, isolation, and capture. First described in 1869,[4] CTC may be obtained from phlebotomy samples in a routine clinical practice setting. Initial studies of CTC in prostate cancer focused on detection of tumor cells using a reverse-transcription polymerase chain reaction (RT-PCR) based assay for the messenger RNA (mRNA) for PSA, also called kallikrein-related peptidase 3 (KLK3), in the mononuclear cell fraction of the blood that are presumed to be from CTC.[5] To improve RT-PCR detection in peripheral blood, additional genes, highly expressed in tumor tissue and not expressed in peripheral blood nucleated cells (PBMC), have been studied as biomarkers to detect minimal residual or recurrent disease, such as prostate-specific membrane antigen, or markers of epithelial mesenchymal transition, or stem-cell origin.[10,11]

Thus, there is a critical unmet need in prostate cancer drug development and treatment for outcome measures that reflect clinical benefit.

SUMMARY OF THE INVENTION

Disclosed herein is the development and analytical validation of a method using an RT-PCR platform to predict sensitivity to dasatinib therapy based on the expression of 7 genes, TACSTD2, TSPAN8, COL3A1, SPOCK1, SFN, KRT7, and S100A2 in circulating tumor cells.

In one aspect, the invention relates to a method for determining the likelihood of prostate cancer response to treatment with dasatinib comprising: (a) measuring the expression levels of RNA transcripts of TACSTD2, TSPAN8, COL3A1, SPOCK1, SFN, KRT7, and S100A2, or their expression products, in circulating tumor cells obtained from a subject; (b) calculating a sensitivity score for said subject by weighting the measured expression levels of individual genes by contribution to dasatinib sensitivity; and (c) creating a report providing the score; wherein a score is indicative of <60 indicates the likelihood that said subject will respond to dasatinib therapy.

In a related aspect, the invention relates to a method for guiding treatment options for a prostate cancer patient, the method comprising measuring the expression levels of RNA transcripts of TACSTD2, TSPAN8, COL3A1, SPOCK1, SFN, KRT7, and S100A2, or their expression products, in circulating tumor cells obtained from the patient; (b) calculating a sensitivity score for said subject and recommending treatment with dasatinib when the sensitivity score for said patient is <60.

In one aspect, the invention relates to a method of predicting responsiveness of a prostate cancer patient to treatment with dasatinib, the method comprising: (a) obtaining circulating tumor cells (CTC) from a blood sample from the patient; (b) using fluidic real time PCR, assessing the expression level of each of the genes TACSTD2, TSPAN8, COL3A1, SPOCK1, SFN, KRT7, and S100A2 in the CTC; (c) using values for the expression level of each of the genes to calculate a score for said subject using the equation:

$$SCORE_{CT} = 100000 \times \left[ \left( 0.00657 \times \log_2\left(\frac{2^{-COL3A1_{CT}}}{2^{-GAPDH_{CT}}}\right) \right) - \left( 0.127 \times \log_2\left(\frac{2^{-KRT7_{CT}}}{2^{-GAPDH_{CT}}}\right) \right) - \left( 0.00246 \times \log_2\left(\frac{2^{-SFN_{CT}}}{2^{-GAPDH_{CT}}}\right) \right) - \left( 0.206 \times \log_2\left(\frac{2^{-S100A2_{CT}}}{2^{-GAPDH_{CT}}}\right) \right) + \left( 0.000893 \times \log_2\left(\frac{2^{-SPOCK1_{CT}}}{2^{-GAPDH_{CT}}}\right) \right) - \left( 0.0838 \times \log_2\left(\frac{2^{-TACSTD2_{CT}}}{2^{-GAPDH_{CT}}}\right) \right) + \left( 0.525 \times \log_2\left(\frac{2^{-TSPAN8_{CT}}}{2^{-GAPDH_{CT}}}\right) \right) - 1835 \right] \div 4938$$

and (d) determining that the patient will respond to treatment with dasatinib if the score obtained from the equation is <60.

In another related aspect, the invention relates to primer/probe sets for determining the expression level of genes TACSTD2, TSPAN8, COL3A1, SPOCK1, SFN, KRT7, and S100A2, as well as kits containing primers and probes for each of the genes of the 7-gene panel for practicing the invention. Kits of the invention may also include primers and probes for the determination of expression levels of control or reference genes, for example, so-called housekeeping genes such as GAPDH. In addition to primers and probes, such kits would optionally contain other reagents for performing PCR.

BRIEF DESCRIPTION OF THE DRAWINGS

FIG. 12 shows the relationship between the differential expression of the 7-gene panel between a dasatinib sensitive cell line, PC3, and a dasatinib resistant cell line, VCaP. Relative expression of each gene was normalized to the expression of PC3 or VCaP.

DETAILED DESCRIPTION OF THE INVENTION

Figure 1:
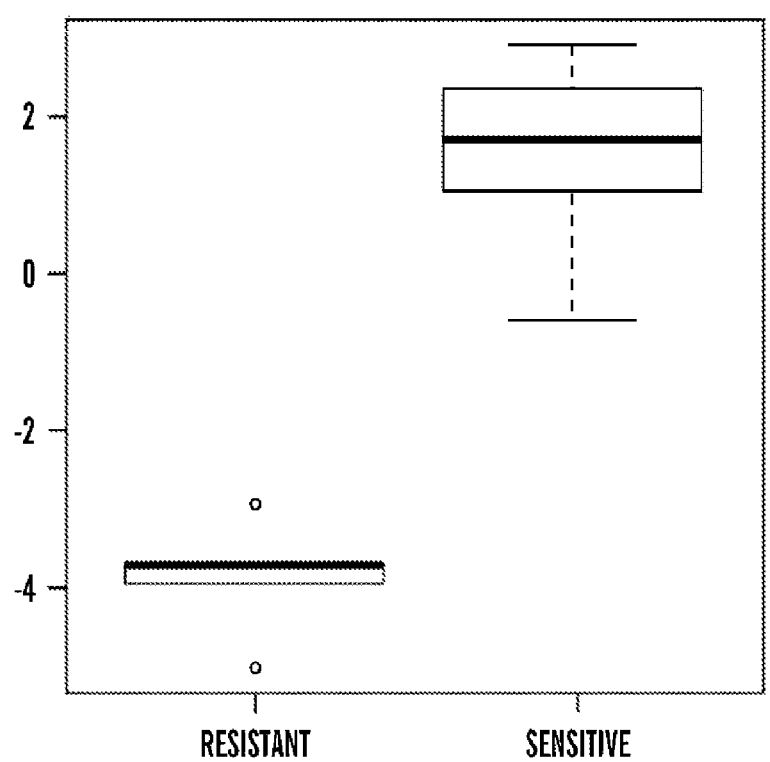
FIG. 1 is a boxplot showing separation of dasatinib resistant and dasatinib sensitive cells with respect to the expression levels of a 7 gene panel in 16 prostate cancer cell lines, using sensitivity scores calculated from Eqn. 1 (below). Log 2 absolute expressions were used for the calculation of the Affymetrix sensitivity scores shown in the boxplot.

All publications, patents and other references cited herein are hereby incorporated by reference in their entirety into the present disclosure.

In practicing the present invention, many conventional techniques in microbiology, cell biology and molecular biology are used, which are within the skill of the ordinary artisan. Some techniques are described in greater detail in, for example, Molecular Cloning: a Laboratory Manual 3rd edition, J. F. Sambrook and D. W. Russell, ed. Cold Spring Harbor Laboratory Press 2001, the contents of this and other references containing standard protocols, widely known to and relied upon by those of skill in the art, including manufacturers' instructions are hereby incorporated by reference as part of the present disclosure.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Abbreviations Used Herein:
COL3A1: collagen, type III alpha 1
CRPC: castrate-resistant prostate cancer
CT or Ct: cycle threshold
CTC: circulating tumor cell
GAPDH: glyceraldehyde-3-phosphate dehydrogenase, a housekeeping gene
KRT7: keratin 7 (CK-7), a type II keratin specifically expressed in the simple epithelia of internal organs and blood vessels
Lactase dehydrogenase: LDH
PBMC: peripheral blood mononuclear cells
S100A2: codes for a calcium binding protein of the same name
SFN: a member of the 14-3-3 family of highly conserved dimer proteins
SPOCK1: codes for the proteoglycan Testican-1 protein
TACSTD2: tumor-associated calcium signal transducer 2 (TACSTD2) is a cell surface receptor overexpressed in many types of tumors, particularly in colorectal, ovarian and bladder cancers.

TSPAN8: the gene responsible for the formation of the membrane protein, tetraspanin 8 (also known as CO-029 and TM4SF3).

The term "primer" as that term is known in the art refers to an oligonucleotide that is complementary to a particular nucleic acid sequence of a template and is capable of acting as a point of initiation of extension with a polymerase under suitable PCR conditions and when used in suitable PCR primer pairs, will produce an amplicon of the target. The primer is preferably single stranded but can also be double stranded. If double stranded, the primer is first treated to separate its strands before being used to prepare extension products. Preferably, the primer is an oligodeoxyribonucleotide. The exact number of nucleotides in the primers will depend on many factors, including temperature, source of primer and the use of the method. The PCR primers of the present invention have about 18 to 25 nucleotides but can contain more or less. Methods for the design and synthesis of PCR primers are readily known in the art.

The terms "predict," "predictive" and "prediction" refer to the likelihood that a patient will have a particular clinical outcome, whether positive or negative, following surgical removal of the primary tumor. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen. The prediction may include prognostic factors.

The term "probe" refers to a single-stranded nucleic acid molecule that can base pair with a complementary single stranded target nucleic acid to form a double-stranded molecule. As the term is known in the art, the term "oligonucleotide" refers to a nucleic acid, generally of at least 18 nucleotides, that is hybridizable to a genomic DNA molecule, a cDNA molecule, a plasmid DNA or an mRNA molecule. Labeled oligonucleotides can be used as probes to detect the presence of a nucleic acid.

The present invention provides a gene expression profile and methods of applying it to identify those patients who are likely to respond to treatment with dasatinib (these patients are referred to as "responders"), as well as those patients who are not likely to benefit from such treatment (these patients are referred to as "non-responders"). The present invention allows a treatment provider to identify patients, prior to administration of the agent, who are likely to be benefit from dasatinib treatment, and those who are not likely to respond to such treatment, thereby eliminating exposure to ineffective treatment.

The 7-gene expression profile (GEP) consists of the following genes: TACSTD2, TSPAN8, COL3A1, SPOCK1, S100A2, KRT7, and SFN. TaqMan assays, spanning exon-intron junctions and optimized for reverse transcription and PCR, were purchased from Applied Biosystems (Life Technologies, Grand Island, N.Y.) such as for KLK3 (cat# Hs03063374_m1), KLK2 (cat# Hs00428383_m1), HOXB13 (cat# Hs00197189_m1), GHRL2 (cat# Hs00227745_m1), and FOXA1 (cat # Hs00270129_m1). Primers and probes suitable for the detection of expression of each of the genes in the sensitivity profile are in some instances commercially available or may be synthesized in accordance with methods known in the art; other variants exist which can be readily ascertained by reference to an appropriate database such as NCBI Entrez, and these variants are encompassed by the present invention. Additionally, the gene signature may further include reference or control genes, for example, a housekeeping gene such as glyceraldehyde-3-phosphate dehydrogenase (GAPDH). Other examples of housekeeping genes include NKIRAS1, ZNF79, BCL10, and CD45.

The present invention provides a mechanism for determining responsiveness of a prostate cancer patient to treatment with a Src tyrosine kinase inhibitor such as dasatinib. Some of the advantages of such a method include: convenient and relatively non-invasive procurement of specimen material for testing, the ability to tailor treatment to the individual patient and also to eliminate non-responders from clinical trials to determine the efficacy of dasatinib.

Isolation of Circulating Tumor Cells (CTC)

The expression level of each of the 7-gene panel in circulating tumor cells from the patient provides the starting point for predicting responsiveness to dasatinib. In one embodiment, circulating tumor cells are obtained by collecting a blood sample from the patient and recovering the EpCAM$^+$, CD45$^-$ CTCs using flow cytometry. RNA is extracted from the CTCs to determine expression levels of a seven gene panel informative of dasatinib sensitivity: TACSTD2, TSPAN8, COL3A1, SPOCK1, SFN, KRT7, S100A2. The sample may be analyzed for gene expression of one or more genes in a signature using methods known to those of skill in the art including, but not limited to, PCR (polymerase chain reaction); RT-PCT (reverse transcriptase-polymerase chain reaction); quantitative PCR, etc.

Additionally, the expression levels of at least one of known "housekeeping genes" is determined for normalization of the values obtained for the seven sensitivity/resistance-selective genes. In one embodiment, glyceraldehyde-3-phosphate dehydrogenase (GAPDH) is used.

In one embodiment, an enriched population of CTC is obtained as follows. Blood from the patient is collected into a ethylene-diaminetetraacetic acid (EDTA)-containing blood collection tube. Peripheral blood mononuclear cells are recovered following centrifugation of the anti-coagulated blood on a density gradient, such as FICOLL™. These cells are then sorted using flow cytometry to isolate the EpCAM$^+$, CD45$^-$ circulating tumor cells.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.).

As RNA cannot serve as a template for PCR, the first step in gene expression profiling by RT-PCR is the reverse transcription of the RNA template into cDNA, followed by its exponential amplification in a PCR reaction. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Quantitative Real-Time PCR

RNA is then extracted from the circulating tumor cells for quantitative or real-time PCR. Real-time PCR is able to detect sequence-specific PCR products as they accumulate in "real-time" during the PCR amplification process and real-time reverse transcription-PCR (RT-PCR) allows interrogation of the expression level of one gene at a time but with great accuracy and a wide dynamic range.

QRT-PCR (or qPCR) may be used to measure the expression of a plurality of biomarkers. In QRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, which binds to double-stranded DNA. The reaction may also be performed with a fluorescent reporter probe that is specific for the DNA being amplified. The fluorescent reporter probe fluoresces when the quencher is removed during the PCR extension cycle.

Muliplex QRT-PCR may be performed using multiple gene-specific reporter probes, each of which contains a different fluorophore. Fluorescence values are recorded during each cycle and represent the amount of product amplified to that point in the amplification reaction. To minimize errors and reduce any sample-to-sample variation, QRT-PCR is typically performed using a reference standard. The ideal reference standard is expressed at a constant level among different tissues, and is unaffected by the experimental treatment. The level of mRNA in the original sample may be determined using calculations well known in the art.

In certain embodiments, a nanofluidic platform (Fluidigm Corporation, South San Francisco, Calif.) is used to determine the levels of gene expression.

Once the levels of gene expression have been measured, these mRNA levels are inserted into a formula that yields a numerical score, which indicates dasatinib sensitivity/resistance. Examples of how to create a signature score are described herein. The signature score is then correlated with a predicted response to cancer treatment.

Kits

The present invention further comprises assay kits for predicting responsiveness of a patient with prostate cancer to treatment with dasatinib based on a determination of the gene expression profile in a patient's sample, and instructions for performing the assay. The assay may be based on detection of nucleic acids (e.g., using nucleic acid probes specific for the nucleic acids of interest) or proteins or peptides (e.g., using antibodies specific for the proteins/peptides of interest). A kit of the invention typically comprises a plurality of agents for measuring the expression of a plurality of genetic biomarkers including, for example, an array of polynucleotides complementary to the mRNAs (or cDNAs) of the biomarkers. In one embodiment, the agents in the kit for measuring biomarker expression may comprise a plurality of PCR probes and/or primers for quantitative PCR. In addition to primers and probes for detecting expression of the 7-gene panel, the kit may optionally contain primers and probes for determining the expression level of one or more housekeeping genes, such as GAPDH.

The following examples are provided in order to demonstrate and further illustrate certain embodiments and aspects of the present invention and are not intended to be construed as limiting the scope thereof.

EXAMPLES

Determination of a Dasatinib Sensitivity Gene Panel

To determine the most robust and clinically viable gene panel for predicting dasatinib sensitivity, data acquired from a study conducted by Wang et al., in which the expression of 22,278 genes in 16 prostate cancer cell lines treated with dasatinib were quantified before and after treatment using Affymetrix microarray chip analysis was used.

A primary screen was first used against the data to select for post-normalized prostate-enriched genes determined through assessment of tumor profiles compiled by the Novartis BIO-GPS Portal database, which had relative expression values of log 2 fold ≥2 relative to whole blood. Using 1362 genes fitting this qualification, parameters for individually differentially expressed genes across sensitive and resistant samples were narrowed using a modified two-sample t-test, in which a shrinkage variance estimate was used to obtain stable inference for the small sample size study. The significantly differentially expressed genes were found after sorting their respective p-values and controlling the false positive rate (FDR)<0.01.

A multivariate gene expression logistic regression model was developed to predict sensitivity to dasatinib treatment in cell lines. An elastic net algorithm, a penalized regression technique, allowed for the incorporation of multiple correlated genes to identify the relevant biomarkers. After setting penalty parameters applied to our genes, the final established panel was comprised of the following seven genes: TACSTD2, TSPAN8, COL3A1, SPOCK1, SFN, KRT7 and S100A2.

A quantitative sensitivity score based on the expression levels of this 7-gene panel is given in Eqn. 1. The candidate models were measured for model prediction accuracy using three statistical tests: C-index, Nagelkerke r-square, and the Brier Score. Using this 7-gene model, we achieved perfect discriminatory power (C-index), high explained variation (r-square), and high calibration (Brier Score). Analyses for the determination of the gene panel can be seen in FIG. 1 and Table 1.

TABLE 1

Predictive power of the 7 gene panel for dasatinib sensitivity.

| Genes | C_index | Likelihood Ratio R2 | Brier Score |
|---|---|---|---|
| 7 gene model | 1 | 0.84 | 0.013 |

All statistics done by Glenn Heller of the Department of Biostatistics and Epidemiology at Memorial Sloan-Kettering Cancer Center From the literature, the following is known about the genes of the 7-gene panel for dasatinib sensitivity.

TROP-2, tumor-associated calcium signal transducer 2 (TACSTD2) is a cell surface receptor overexpressed in many types of tumors, particularly in colorectal, ovarian and bladder cancers[1-5]. It has been established as a cancer-related gene[1], and has been linked to cancer aggressiveness and poor prognosis[1,6,7]. Its overexpression in metastatic tissue makes it an therapeutic target under investigation[7]. Upregulation of TACSTD2 was found in a study by Guerra et al. to be necessary and sufficient to stimulate tumor growth[8,9]. In addition, TACSTD2 expression appears to be dependent on a many transcription factors, including ERK and FOXP3 (the NFkappaB pathway)[8]. CG-5 and glucose deprivation of LNCaP cells downregulated methylated tumor/invasion-promoting genes, including CD44, S100A4, and TACSTD2[10]. Contradictorily, TACSTD2 was found to be hypermethylated in 17% of prostate tumors in a study by Ibragimova et al[11], suggesting the regulation of TACSTD2 expression may be case-dependent.

TSPAN8, the gene behind the formation of the membrane protein, tetraspanin 8 (also known as CO-029 and TM4SF3), has been found to promote tumor progression[12], as well as induce angiogenesis in tumors through an exosomal pathway[12-14]. Tetraspanin 8 regulates cell motility and survival, and overexpression of tetraspanin-8 has been shown to promote migration, invasion, and metastasis. It has been suggested that tetraspanin 8 is associated with an increased resistance to apoptosis, likely through an EPCAM-claudin 7 pathway[12].

The SPOCK1 gene codes for the proteoglycan Testican-1 protein, a protein with largely unknown function, but it has been suggested that its function may be related to protease inhibition15. Wlazlinski et al. observed SPOCK1 overexpression in prostate cancer tissue samples via RT-PCR15, associated with changes in the expression of other ECM genes including fibulin, and may represent changes in the extracellular environment brought about by ERG oncogenic activations16.

SFN, a member of the 14-3-3 family of highly conserved dimer proteins, has been shown to interact with over 100 other cellular proteins, suggesting its role as biochemical regulator[17-19]. 14-3-3sigma (stratifin) is highly expressed in normal prostate epithelium[20], but appears to be lost early in prostate and breast carcinoma by DNA hypermethylation-mediated silencing[20,21].

The S100A2 gene, which codes for a calcium binding protein of the same name, is involved in cell proliferation and migration[22], and is considered a tumor suppressor[23-25]. It is often down-regulated in carcinoma, in particular within the epithelial tissue of tumors[26].

KRT7, the gene for keratin 7 (CK-7), a type II keratin specifically expressed in the simple epithelia of internal organs and blood vessels, is underexpressed in prostate cancer through hypermethylation, much like SFN11. Ibragimova et al. suggests that hypermethylation of KRT7 may provide a growth advantage through cell-cell adhesion11. A recent study reported a subgroup of clear cell renal cell carcinomas with KRT7 expression being associated with genetic stability, a distinct global expression signature, and a more indolent clinical course27. Dozmorov et al. observed prostate cell line-specific expression of KRT7, as uniquely expressed in androgen insensitive PC3 but not in LNCaP.

The COL3A1 gene, for collagen, type III alpha 1, a collagen strongly expressed in connective tissue, is a major component of the extracellular matrix and mutations within the COL3A1 gene have been known to cause type IV Ethlers-Danlos syndrome28. COL3A1 has been observed to be overexpressed in metastatic prostate cancer29.

Processing of Affymetrix GeneChip.CEL Data

Raw Affymetrix GeneChip.CEL data from the NCBI GEO database (GSE9633) were processed using the affy( ) packages from BioConductor for the R console, adapted by the computational biology department at MSKCC. (http://www.bioconductor.org/packages/release/bioc/html/affy.html) The script used can be found at Microarray/ProcessAffyRscript.doc. The script performs a GC-RMA normalization and mas5 summarization on the data, outputting a spreadsheet containing log 2 expressions for each gene as well as a spreadsheet for probe present/absent indicators.

Processing of Fluidigm qPCR data

CT values with each gene/cell line combination in replicates in eight were obtained for 7 cell lines (PC3, VCaP, LNCaP, 22RV1, CWR, LAPC4 and MDACaP2b), in summarized form from Fluidigm.

The coefficient of variation (C.O.V.), a standard measure of reproducibility, was measured between each eight replicate-set of PCR CT data, calculated as (standard deviation)/(mean) within each set, and is reported as a percent variation to 3 significant digits in Table 2.

TABLE 2

Coefficient of Variation in 7-cell lines CT data

| C.O.V.(%) | VCAP | LNCAP | CWR | PC3 | LAPC4 | MDA | 22RV1 |
|---|---|---|---|---|---|---|---|
| TACSTD2 | 3.09 | 4.61 | 1.77 | 2.35 | 11.33 | 3.32 | 5.17 |
| TSPAN8 | 1.74 | 3.97 | 5.74 | 0.69 | 6.86 | 4.44 | 4.59 |
| COL3A1 | 1.83 | 3.10 | 1.54 | 1.59 | 3.92 | 2.59 | 5.33 |
| SPOCK1 | 2.68 | 5.44 | 1.42 | 2.01 | 2.82 | 2.67 | 4.60 |
| S100A2 | 10.3 | 8.72 | 3.41 | 0.14 | 7.66 | 8.41 | 2.83 |
| KRT7 | — | — | 11.80 | 1.42 | 9.31 | 16.08 | 4.24 |
| SFN | 1.73 | 4.24 | 2.87 | 1.64 | 4.95 | 1.36 | 3.92 |
| GAPDH | 5.43 | 6.40 | 1.61 | 1.66 | 8.84 | 7.22 | 7.65 |

Within the qPCR data, the source of the greatest variation in the data is the KRT7 gene, with % variation near 16%. Most of the CT data stays within ±10%.

Finding Relative Expressions of Affymetrix and RT-PCR to GAPDH-Making the Connection Between Platforms To analyze whether dasatinib sensitivity using our gene panel could be detected using a more powerful and sensitive RT-qPCR platform (Fluidigm Dynamic Assay), relative expression of the gene panel in both platforms was calculated and compared to observe any similarities. Because the CWR and LAPC4 cell lines were not studied in Wang et al., there is no Affymetrix microarray data for the two cell lines, and the qPCR data for these cell lines was not useful for comparing the platforms. However, the remainder 5 cell lines were used.

Figure 2:
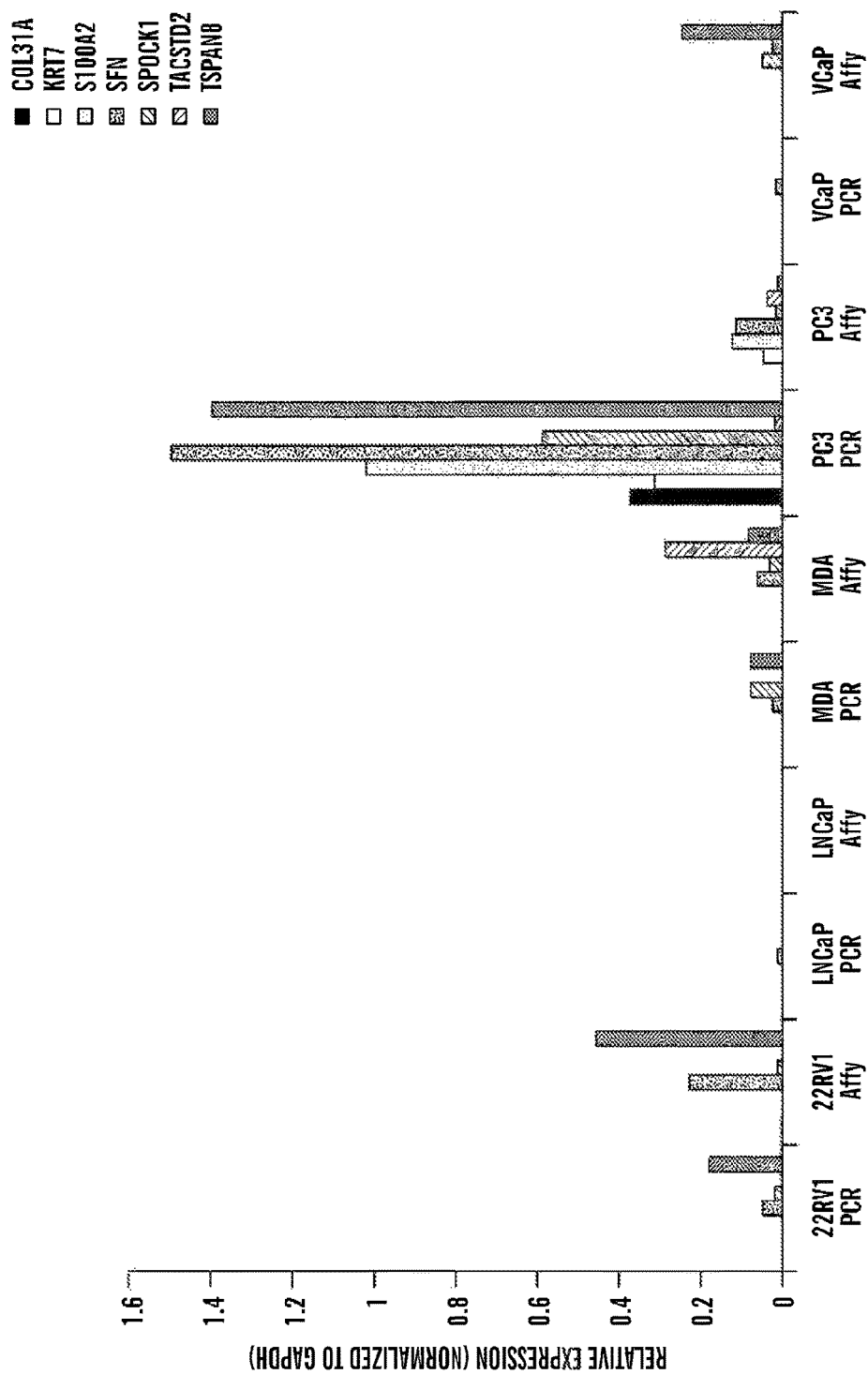
FIG. 2 shows the relative expression of the dasatinib signature gene panel in 5 cell lines as a bar graph showing a comparison of 2^-dCt relative expressions (normalized to GAPDH) in RT-PCR and relative expressions to GAPDH in Affy. 22RV1 shows a clear connection, although MDA and PC3 do not.
Figure 3B:
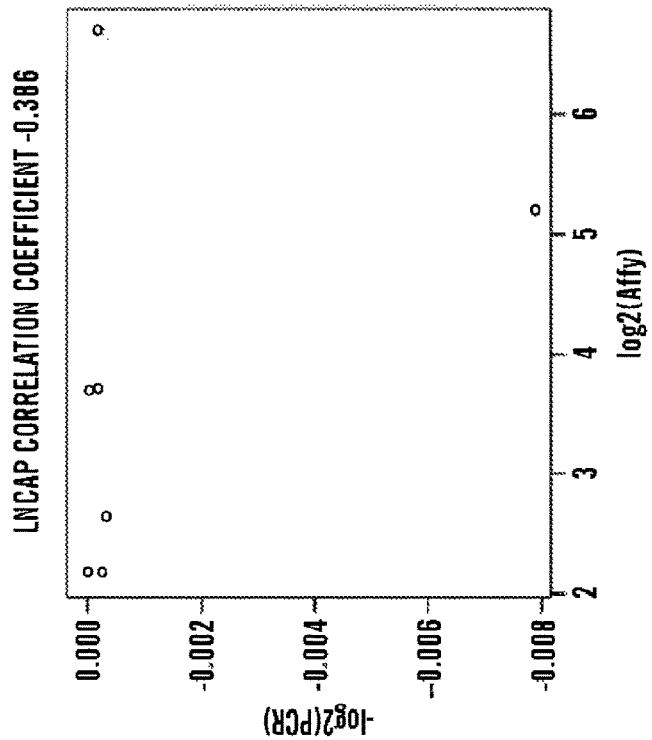
FIG. 3A-E shows Affymetrix vs. PCR fold-change graphs created using merged 2011 and 2012 CT data. A Pearson linear correlation coefficient was calculated to determine the agreement between the platforms. As supports FIG. 1, the 22RV1 Pearson's correlation is 0.931, supporting strong correlation between RT-PCR results and the microarray data from Wang. However, for cell lines like PC3, it is possible that the results have differed due to batch-dependent expression.
Figure 3A:
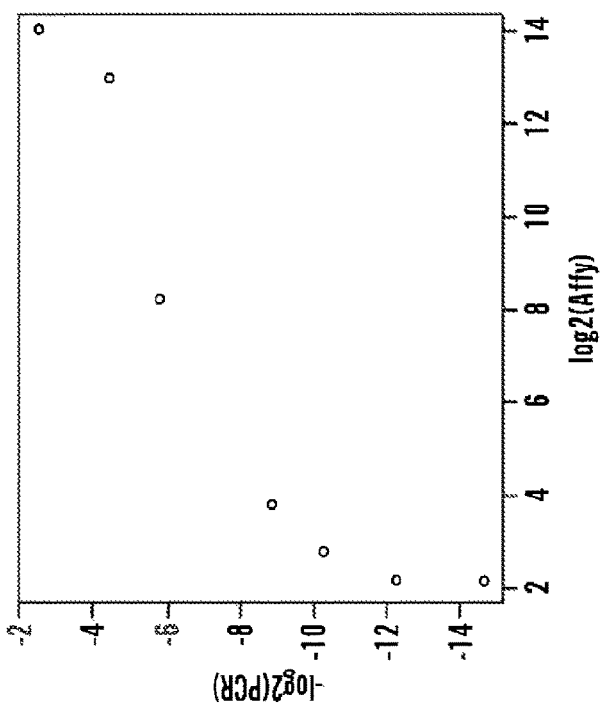
Figure 3D:
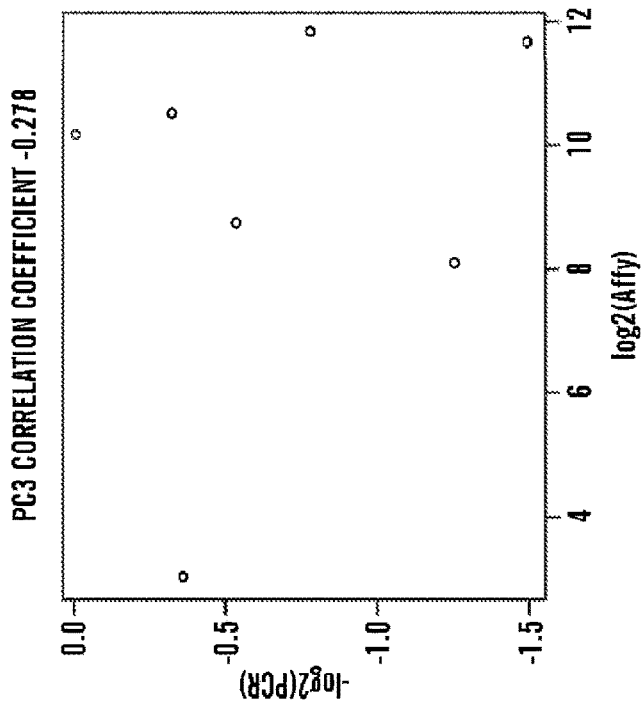
Figure 3C:
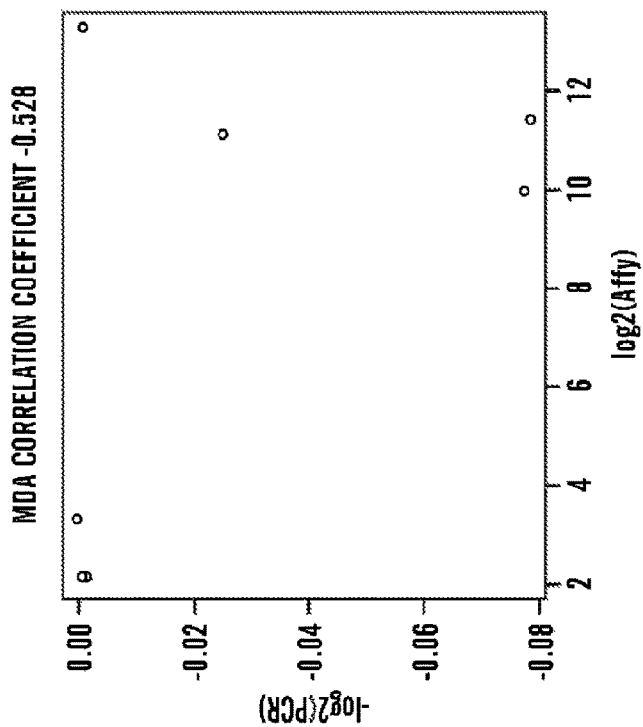
Figure 3E:
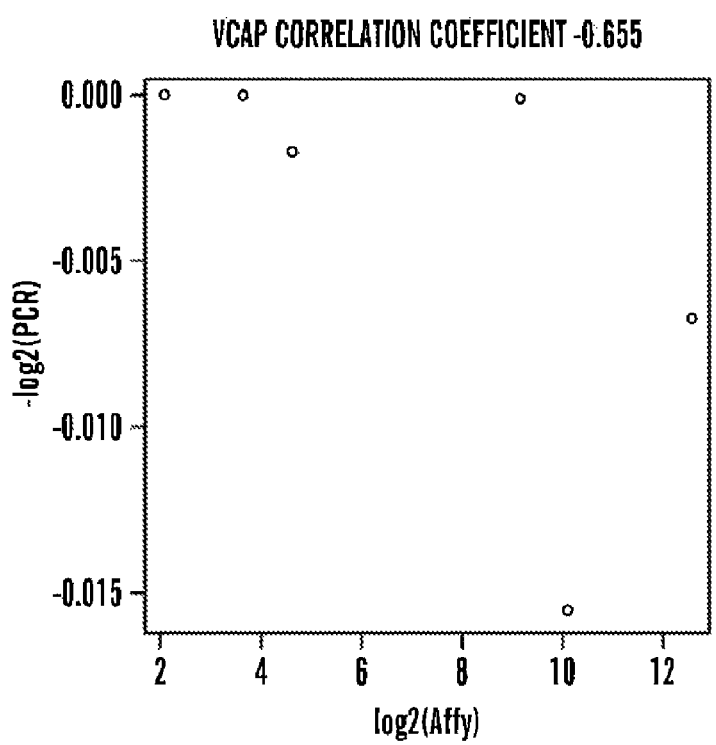

Relative expression of the gene panel with reference to the housekeeping gene GAPDH was determined for the PC3, VCAP, LNCAP, MDA, and 22RV1 cell lines for both the Affymetrix data acquired from Wang et al. (NCBI GEO Database, GSE 9633)[30], and using cycle threshold (CT) values from qPCR run at MSKCC, expressed to 2-ΔCT values, and compared as shown in FIG. 2. Glyceraldehyde-3-phosphate dehydrogenase (GAPDH), was chosen as the housekeeping gene (HKG), due to its uniform expression across cell lines and its common use as a HKG in PCR comparative CT analysis[31].

For Affymetrix data, a 2^x transform was first applied in order to obtain absolute expressions from the $\log_2$ expressions returned by mas5 summarization. Afterwards, within each cell line, the absolute expression of each gene in our panel was divided by that of GAPDH.

For PCR, the comparative CT method was applied to obtain 2^-dCT relative expressions, calculated as:

$$\frac{2^{-CT_{GENE}}}{2^{-CT_{HKG}}} = 2^{-\Delta CT} Expression_{Gene} = 2^{-(CT_{Gene}-CT_{HKG})}$$

where "Gene" is the gene in question, and "HKG" is the housekeeping gene, or GAPDH. Next, combining previous qPCR runs, we obtained a more complete data set with expressions for PC3, LNCAP, and VCAP. Due to the need to summarize between 8 or more replicates for each gene/cell line combination, two methods, A and B below, were used to perform the 2-ΔCT, with the same results.

A. The summary data was formatted into a tab-delimited text DataAssist PCR format (not Fluidigm), then the ddCt( ) script was applied, provided by Bioconductor (at url bioconductor.org/packages/release/bioc/html/ddCt.html). A 2^-transform was then applied to ΔCT values obtained from the output .csv file to obtain the relative expression, normalized to GAPDH. A comparison of 2^-dCT relative expressions (normalized to GAPDH) in RT-PCR and relative expressions to GAPDH in Affymetrix are shown in FIG. 2.

B. Manually calculating the $2^{-\Delta CT}$ relative expressions for each gene/cell line combination involves subtracting each replicate's GAPDH CT from the Gene CT, then taking the mean of all replicate's ΔCT values found. Next, the same 2^-transform applied above was applied to obtain final relative expressions, normalized to GAPDH.

Using merged 2011 and 2012 CT data, Affymetrix versus PCR fold-change graphs were created (see FIGS. 3A-E). A Pearson linear correlation coefficient was calculated to determine the agreement between the platforms. As supports FIG. 1, the 22RV1 Pearson's correlation was 0.931, supporting a strong correlation between the RT-PCR results and the microarray data from Wang.

For patient samples, a third step was required for processing of the qPCR data from profiling of CTCs. This involves the correction for WBC contamination by CD45. The above calculations are done for each WBC and CTC group from patients. Afterwards, the following calculation is performed for each gene:

$$Expression_{corrected} = Expression_{CTC} - \left(\frac{CD45_{CTC}}{CD45_{WBC}}\right) Expression_{WBC}$$

Use of a Quantitative Formula to Predict Sensitivity

In order to reliably interpret expression values of the 7-gene panel, a quantitative formula was derived based on the individual contributions of each gene to the predictive power of the entire gene panel (Eqn. 1).

Equation 1: Sensitivity Score for Affymetrix Microarray Log 2 Absolute Expressions.

$$SCORE_{Affy} = (0.114*TACSTD2_{Affy}) - (0.703*TSPAN8_{Affy}) - (0.036*COL3A1Affy - 0.002*SPOCK1Affy + 0.022*SFNAffy + 0.514*KRT7Affy + 0.518*S100A2Affy \quad \text{Eqn.1}$$

The panel scores were used to characterize three states: "sensitive", "resistant", and "indeterminate". A positive score indicates predicted sensitivity, a negative score indicates resistance. Importantly, the genes in the positive terms of the formula were selected due to their high expression in sensitive cell lines and low expression in resistant cell lines. Likewise, the genes contributing to negative terms in the score were chosen due to high expression in resistant cell lines but low expression in sensitive cells.

Adapting the Sensitivity Score Equation for RT-PCR

Figure 4:
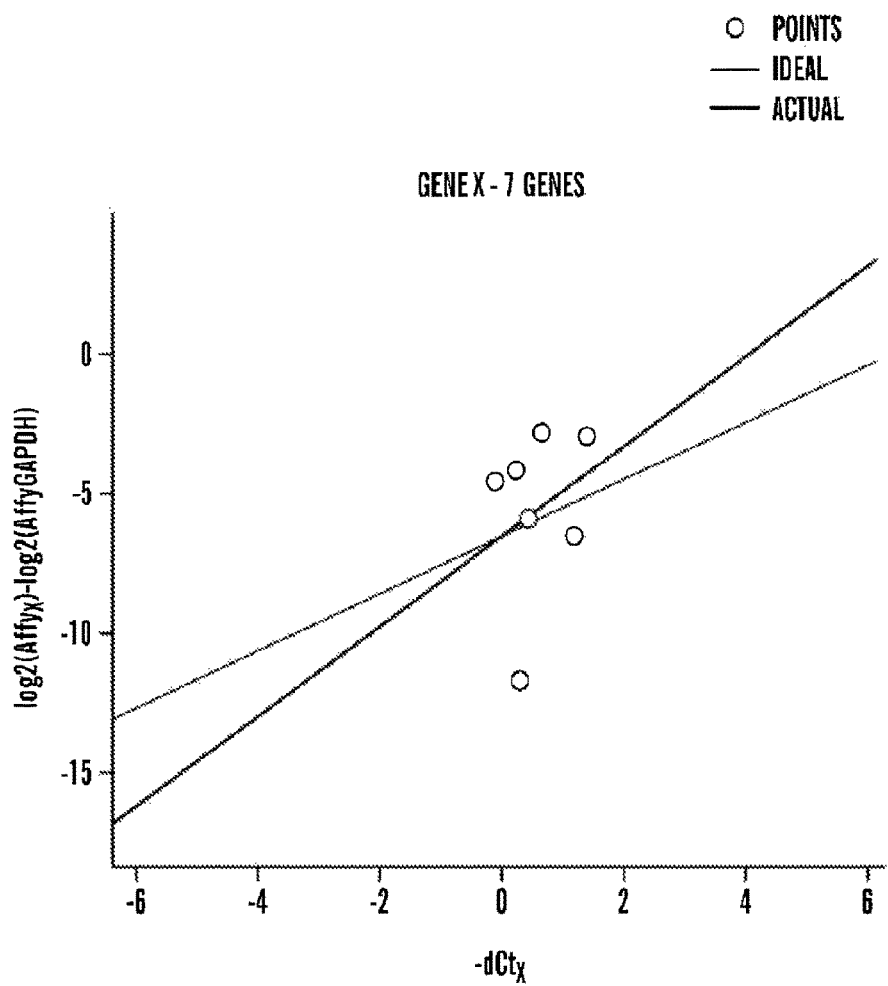
FIG. 4 shows the comparison of the expression of the GAPDH housekeeping gene between the Affymetrix and Fluidigm platforms. Each gene's fold change expression relative to GAPDH is plotted. Ideally, the ratio between relative expression to GAPDH should be identical between the two platforms. The slope of the least squares regression line is 1.58, but would ideally be 1 in a perfect agreement between the PCR and Affymetrix platforms. This indicates that some change to the housekeeping gene occurs between the two platforms, and some alteration of the Affymetrix sensitivity score equation (Eqn. 1) was required before applying it on RT-qPCR data.
Figure 5B:
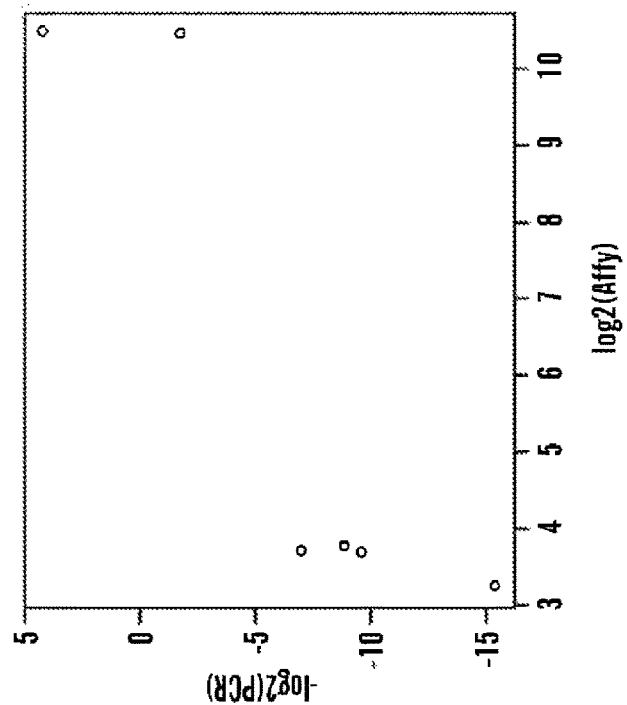
FIGS. 5 A-G are boxplots showing the reference gene (GAPDH) normalized PCR log(2^-dCT)(y-axis) and log 2 Affymetrix expressions (x-axis) for each gene showing all cell lines. Each point (in black) represents a cell line, and genes have varying number of points due to lack of expression data for cell lines. A simple least squares linear regression was performed on the data, and the slope represents the scaling factor (S.F.) for the each gene's coefficient within the original sensitivity score equation for Affymetrix, with reference to the change in GAPDH between the platforms. The correlation coefficients for each graph are shown.
Figure 5A:
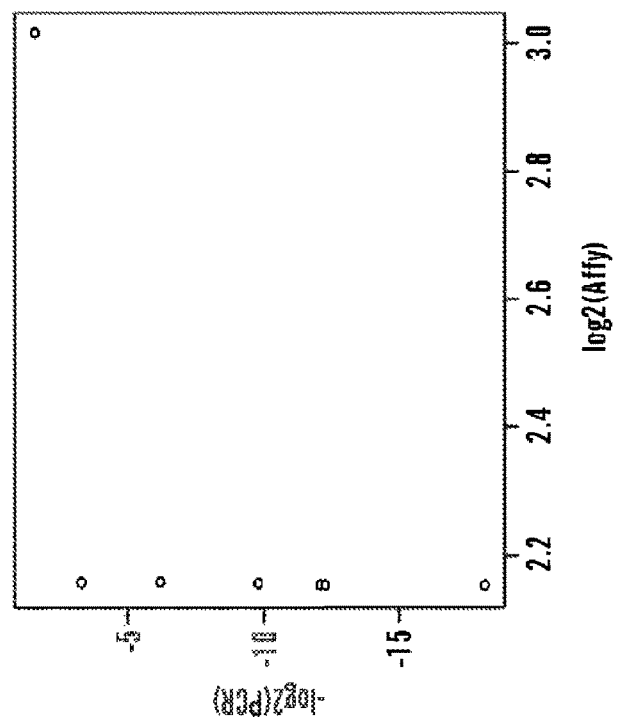
Figure 5F:
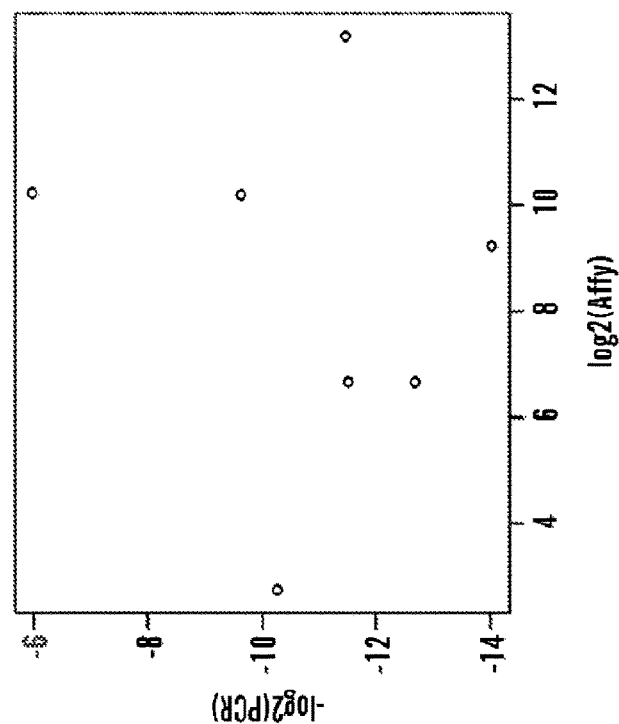
Figure 5E:
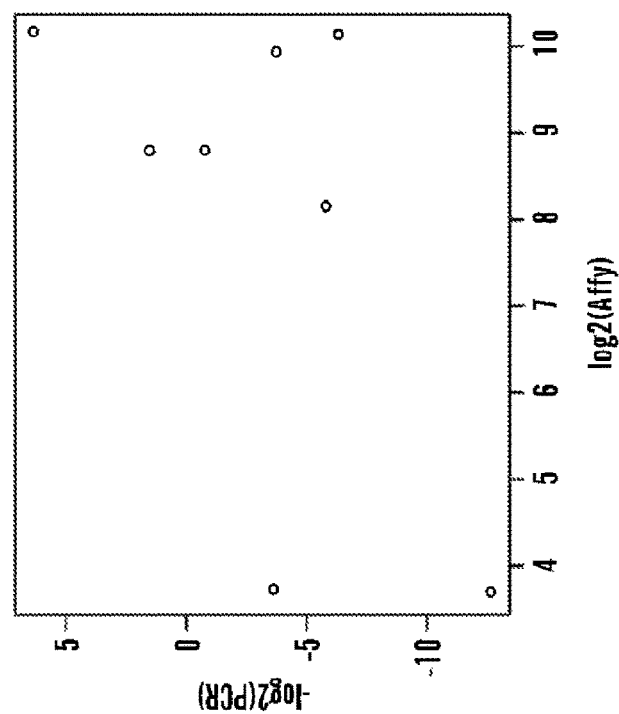
Figure 5G:
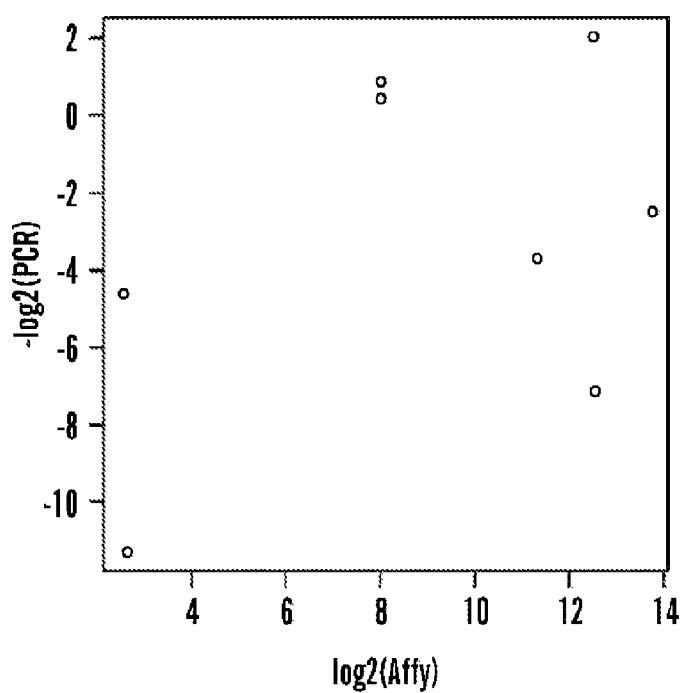

The transformation for each coefficient in the Affymetrix signature score equation to RT-qPCR involved the use of a reference gene. The change in each gene's expression relative to the reference gene from Affymetrix to the Fluidigm RT-qPCR platform was calculated. The reference gene selected was glyceraldehyde-3-phosphate dehydrogenase (GAPDH), for its common use as housekeeping gene and its noted uniformity across cell lines[31]. The change in the reference gene between platforms is shown in FIG. 4.

Each gene's fold change expression relative to GAPDH was plotted. Ideally, the ratio between relative expression to GAPDH should be identical between the two platforms. The slope of the least squares regression line is 1.58, but would ideally be 1 in a perfect agreement between the PCR and Affymetrix platforms. This indicates that some change to the housekeeping gene occurs between the two platforms, and some alteration of the Affymetrix sensitivity score equation (EQn. 1) is required before applying it to RT-PCR data.

To utilize the equation for microarray data for Fluidigm qPCR, a relation in the expression of each gene between the two platforms was required. The relative expression (to GAPDH) of each gene for Affymetrix vs. Fluidigm qPCR in each cell line was compared (FIG. 5A-G), generating Pearson correlation coefficients for each comparison (FIG. 5A-G, Table 3). The relative expressions for qPCR were log 2($2^{-dCT}$) calculated by comparative CT analysis, and the relative expressions for Affymetrix were log(Gene)–log (GAPDH) values from mas5 summarization. The relative expressions used thus represented the fold change between each gene and GAPDH.

Overall, the TACSTD2 gene expression was found to be very inconsistent between the microarray expression observed by Wang et al. and the RT-PCR expression data, with a Pearson correlation coefficient of 0.114. The other genes are moderately correlated between the two platforms, with correlation coefficients given in Table 3.

TABLE 3

Summary of Affymetrix vs. PCR correlation data

| Gene | Scaling Factor (slope) | Correlation Coefficient | Significance of Correlation (p-value) |
|---|---|---|---|
| COL3A1 | −0.183 | −0.675 | 0.0201 |
| KRT7 | −0.247 | −0.887 | 0.474 |
| S100A2 | −0.112 | −0.851 | 0.583 |
| SPOCK1 | −0.397 | −0.410 | 0.523 |
| SFN | −0.446 | −0.565 | 0.384 |
| TACSTD2 | −0.735 | −0.114 | 0.00189 |
| TSPAN8 | −0.747 | −0.436 | 0.283 |

For the genes, we determined the slope of the least squares linear regression line with forced 0 intercept between the relative expression of both platforms, which we termed as the "scaling factor" between the Affymetrix and Fluidigm platforms [Table 3]. This scaling factor was representative of the amount of change in RT-qPCR relative expression in Fluidigm predicted for each incremental change in Affymetrix relative expression.

The coefficients in the sensitivity score equation were weighted based upon relative expression of our gene panel to produce a separation of sensitive and resistant cell lines using Affymetrix microarray data. By determining the scaling factor for each gene's relative expression between the two platforms, the sensitivity score equation utilizing qPCR values can be used in the score calculation if the coefficients are scaled appropriately. By multiplying each coefficient in the score formula for Affymetrix data by the scaling factor for that gene between platforms, we obtained coefficients weighted for RT-qPCR relative expression, which are reported in (Table 4) to three significant digits. An equation using these calculated coefficients (Eqn. 2) was used to calculate RT-qPCR determined sensitivities for the 5 cell lines, and later in CTC of patient samples.

Table 4 shows scaling factors and new coefficients. Affy=$\alpha$*PCR, where $\alpha$ is the scaling factor between platforms. If coefficients in the sensitivity score equation are C, C*Affy=C*($\alpha$*PCR)=C'*PCR, where C' represents the altered coefficient, C'=C*$\alpha$. Thus, New Coeff.=Original Coeff.×Scaling Factor

TABLE 4

Scaling Factors and New Coefficients

| Gene | Orig. Coeff. | Scaling Factor | New Coeff. |
|---|---|---|---|
| COL3A1 | −0.036 | −0.183 | 0.00657 |
| KRT7 | 0.514 | −0.247 | −0.127 |
| S100A2 | 0.518 | −0.112 | −0.0580 |
| SFN | 0.022 | −0.397 | −0.00873 |
| SPOCK1 | −0.002 | −0.446 | 0.000893 |
| TACSTD2 | 0.114 | −0.735 | −0.0838 |
| TSPAN8 | −0.703 | −0.747 | 0.525 |

To finalize the adaptation of the Affymetrix GeneChip signature score to RT-PCR, the coefficients for each gene in the original formula are transformed by their gene's corresponding scaling factor, to obtain the following score formula, using expression values from PCR (Table 2), and obtain the RT-PCR adapted sensitivity score equation.

When used with CT values, the formula is represented as:

Equation 2. Sensitivity Score for RT-PCR $$SCORE_{CT} = 1000 * \left[\left(0.00657 \times \log_2\left(\frac{2^{-COL3A1_{CT}}}{2^{-GAPDH_{CT}}}\right)\right) - \right.$$
$$\left(0.127 \times \log_2\left(\frac{2^{-KRT7_{CT}}}{2^{-GAPDH_{CT}}}\right)\right) - \left(0.00246 \times \log_2\left(\frac{2^{-SFN_{CT}}}{2^{-GAPDH_{CT}}}\right)\right) -$$
$$\left(0.206 \times \log_2\left(\frac{2^{-S100A2_{CT}}}{2^{-GAPDH_{CT}}}\right)\right) + \left(0.000893 \times \log_2\left(\frac{2^{-SPOCK1_{CT}}}{2^{-GAPDH_{CT}}}\right)\right) -$$
$$\left.\left(0.0838 \times \log_2\left(\frac{2^{-TACSTD2_{CT}}}{2^{-GAPDH_{CT}}}\right)\right) + \left(0.525 \times \log_2\left(\frac{2^{-TSPAN8_{CT}}}{2^{-GAPDH_{CT}}}\right)\right)\right]$$

Because the relation of CT and expression is inverse, the scaling factors are negative. Although rescaling the score for final implementation isn't completed, a more negative score indicates sensitivity while a more positive score represents resistance. Using this score on the merged (2011 data and 2012 data) CT results, we calculate the scores of our 7 cell lines, shown in Table 5.

TABLE 5

Scores of cell lines

| Detector | RT-PCR Score | Expected Profile (IC-50[30]) |
|---|---|---|
| 22RV1 | 1487 | Resistant |
| CWR | 3000 | — |
| LAPC4 | −1835 | — |
| LNCAP | −569.9 | Sensitive |
| PC3 | 899.2 | Sensitive |
| VCAP | 2310 | Resistant |
| MDA | 1620 | Resistant |

As a sensitive score has switched signs with the equation in terms of −dCt, the PC3 appears to be resistant, contradicting the expected profile, but upon closer inspection, the PC3 score is the least positive score amongst many resistant profiles. This indicated that a possible rescaling of the score may be necessary.

To confirm, we calculated the scores for the 7 cell lines, this time separating the 2011 and 2012 data sets as we had done in the platform-to-platform transformation. This allows the use of 3 more data points for evaluating the accuracy of our sensitivity score. The scores calculated from the CT of the data are given below in Table 6.

TABLE 6

Scores of 2011 and 2012 data, treated as separate cell lines

| Sample | Score | Expected IC-50 |
|---|---|---|
| 22RV1 (2012) | 1488 | Resistant |
| CWR (2012) | 3000 | — |
| LAPC4 (2012) | −1835 | — |
| LNCAP (2012) | NA | Sensitive |
| LNCAP (2011) | 182.0 | Sensitive |
| MDA (2012) | 1620 | Resistant |
| PC3 (2012) | 946.6 | Sensitive |
| PC3 (2011) | 579.9 | Sensitive |
| VCAP (2012) | NA | Resistant |
| VCAP (2011) | NA | Resistant |

The score for PC3 in this case is again positive, seeming to signify resistance that contradicts its expected sensitive profile, but it also is much less positive than the cell lines with expected IC-50 resistance. This reaffirms the possibility to rescale our score to match with the expected IC-50 profiles.

Worst-Case Accuracy Scenario Profiles

The "NA" in the data set occur from the presence of −999s in dCt values calculated when the CT exceeds the set Fluidigm threshold of 40. To account for this, we substitute the worst-case scenario for accuracy for the −999s in the data to generate scores. For the cell lines with expected resistance and with −999s for genes that contribute to sensitivity, we substitute the −999 with a dCt obtained by using the cycle threshold, 40, as the CT value. This appears to alter the data so that a gene that confers sensitivity that would otherwise have no expression is given an arbitrary expression greater than 0. However, nothing is changed for the −999s in genes that have expected resistant profiles in genes that confer resistance—these cell lines' scores stay undeterminable.

In this sense, the score of the genes with these holes is weighted towards the case of opposite the expected result. The final meaning of this scenario means that if a predicted-resistant cell line still shows a resistance profile after weighting the score for sensitivity, we can be more certain that the cell line is indeed resistant, and vice versa for a sensitive cell line.

TABLE 7

Worst-case scenario determination of possible replacement

| Gene | Contributes to Resistance/Sensitivity in Score | | |
|---|---|---|---|
| COL3A1 | Resistance | | |
| KRT7 | Sensitivity | | |
| S100A2 | Sensitivity | | |
| SFN | Sensitivity | | |
| SPOCK1 | Resistance | | |
| TACSTD2 | Sensitivity | | |
| TSPAN8 | Resistance | | |

| -dCt Data | LNCAP (2012) | VCAP (2012) | VCAP (2011) |
|---|---|---|---|
| COL3A1 | −12.1 | −18.1 | −6.07 |
| KRT7 | −999 | −999 | −6.94 |
| S100A2 | −19.2 | −22.5 | −999 |
| SFN | −6.94 | −9.38 | −1.44 |
| SPOCK1 | −12.6 | −6.24 | 6.41 |
| TACSTD2 | −12.7 | −14.0 | −999 |
| TSPAN8 | −11.4 | −7.18 | 2.12 |

In this case, the dCt values for the KRT7 gene in the VCaP (2012) line, and TACSTD2 and S100A2 in the VCaP (2011) line (in bold) may be changed, pushing the expected-resistant VCaP cell line towards a sensitive score. However, the LNCAP (2012) is unchanged as KRT7 promotes sensitivity, and changing the −dCt from −999 will lead to a best-case scenario. The results of this scenario are given in Table 8.

TABLE 8

Substitution of CT threshold on "NA" values, weighted for worst-case accuracy

| Sample | Score | Expected IC-50 |
|---|---|---|
| 22RV1 (2012) | 1487 | Resistant |
| CWR (2012) | 3000 | — |
| LAPC4 (2012) | −1835 | — |
| LNCAP (2012) | NA | Sensitive |
| LNCAP (2011) | 182.0 | Sensitive |
| MDA (2012) | 1620 | Resistant |
| PC3 (2012) | 946.6 | Sensitive |
| PC3 (2011) | 579.9 | Sensitive |
| VCAP (2012) | 2546 | Resistant |
| VCAP (2011) | 3103 | Resistant |

The results show that using our sensitivity score, even as the VCAP cell line has been induced to become more sensitive, the score is still very positive, indicating resistance to dasatinib. The VCaP (2012) score must be at least 2546, and the VCaP (2011) score must be at least 3103, and would likely give a much more resistant score if the CT-threshold on Fluidigm was set higher. In this way, we give a method of obtaining a score for a data set that would otherwise give an undetermined result.

Figure 6:
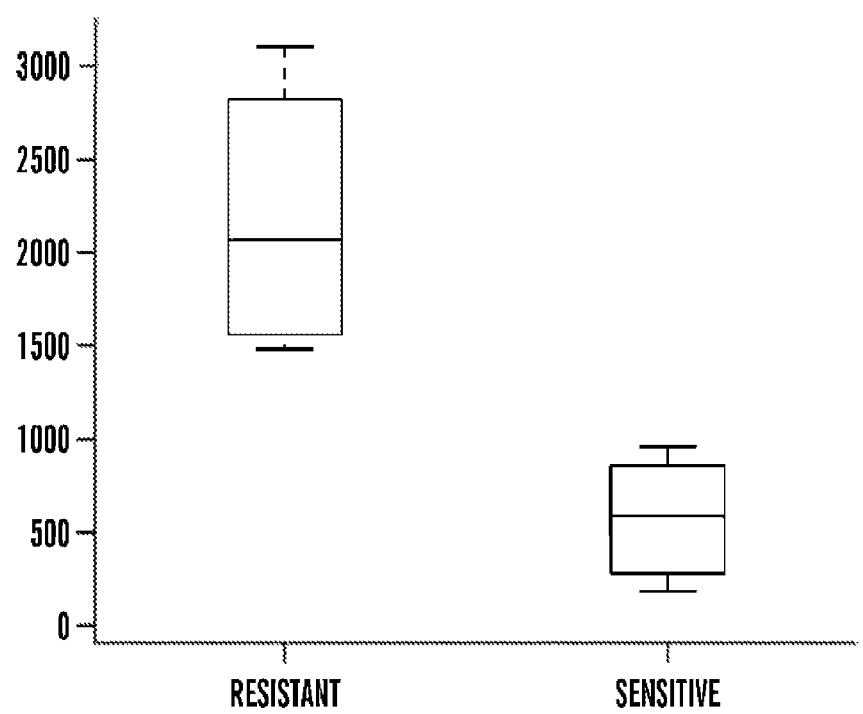
FIG. 6 shows the separation of resistant and sensitive cell lines when scores for cell lines which lack either an expected IC-50 dasatinib sensitivity profile or a definitive score (CWR, APC4, and LNCaP) are excluded.
Figure 7:
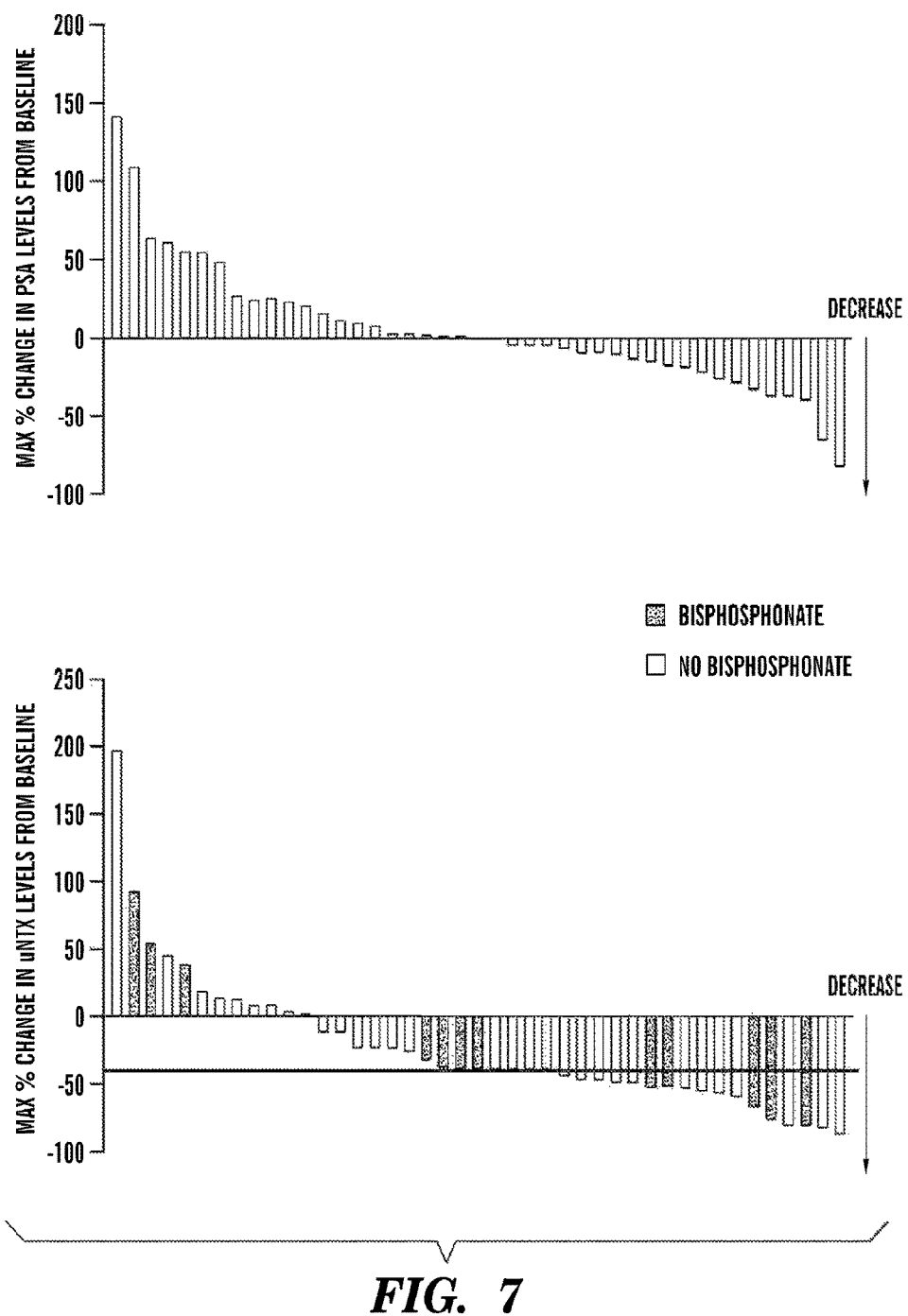
FIG. 7 shows waterfall plots for prostate specific antigen (PSA) (upper panel), and urinary N-telopeptide of type I collagen (uNTX)(lower panel) in CRPC patients treated with dasatinib (100 mg once daily) indicating that the decline in uNTX, indicating anti-resorptive effect, is present in a significantly larger percentage of patients than PSA decline.
Figure 8:
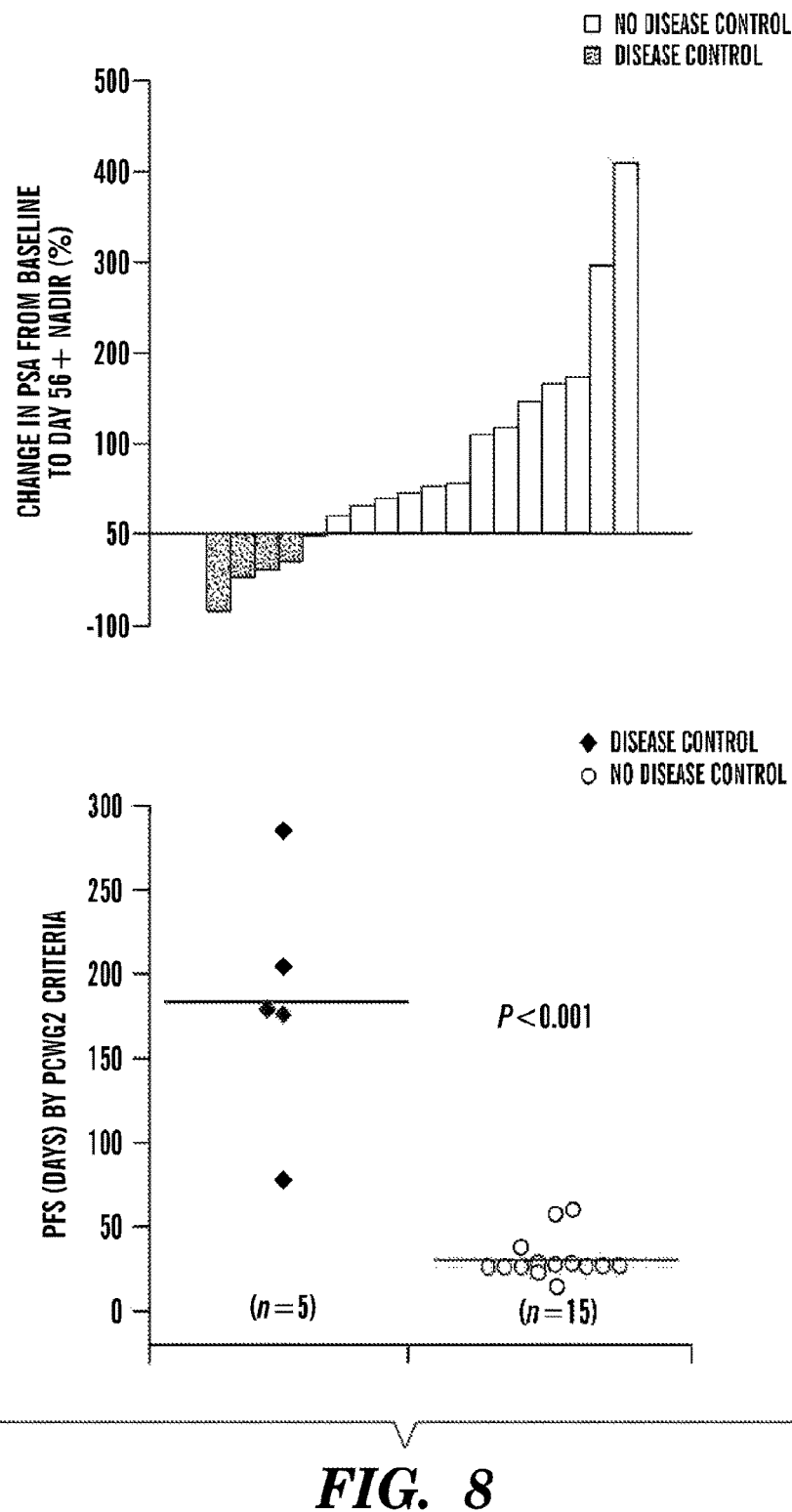
FIG. 8 upper panel shows a waterfall plot of changes in PSA levels among patients with or without disease control on day 56. The lower panel shows that progression free survival (PFS) according to the Prostate Cancer Working Group 2 (PCWG2) criteria in patients with disease control (DC ♦) or who failed to achieve DC (o).
Figure 9:
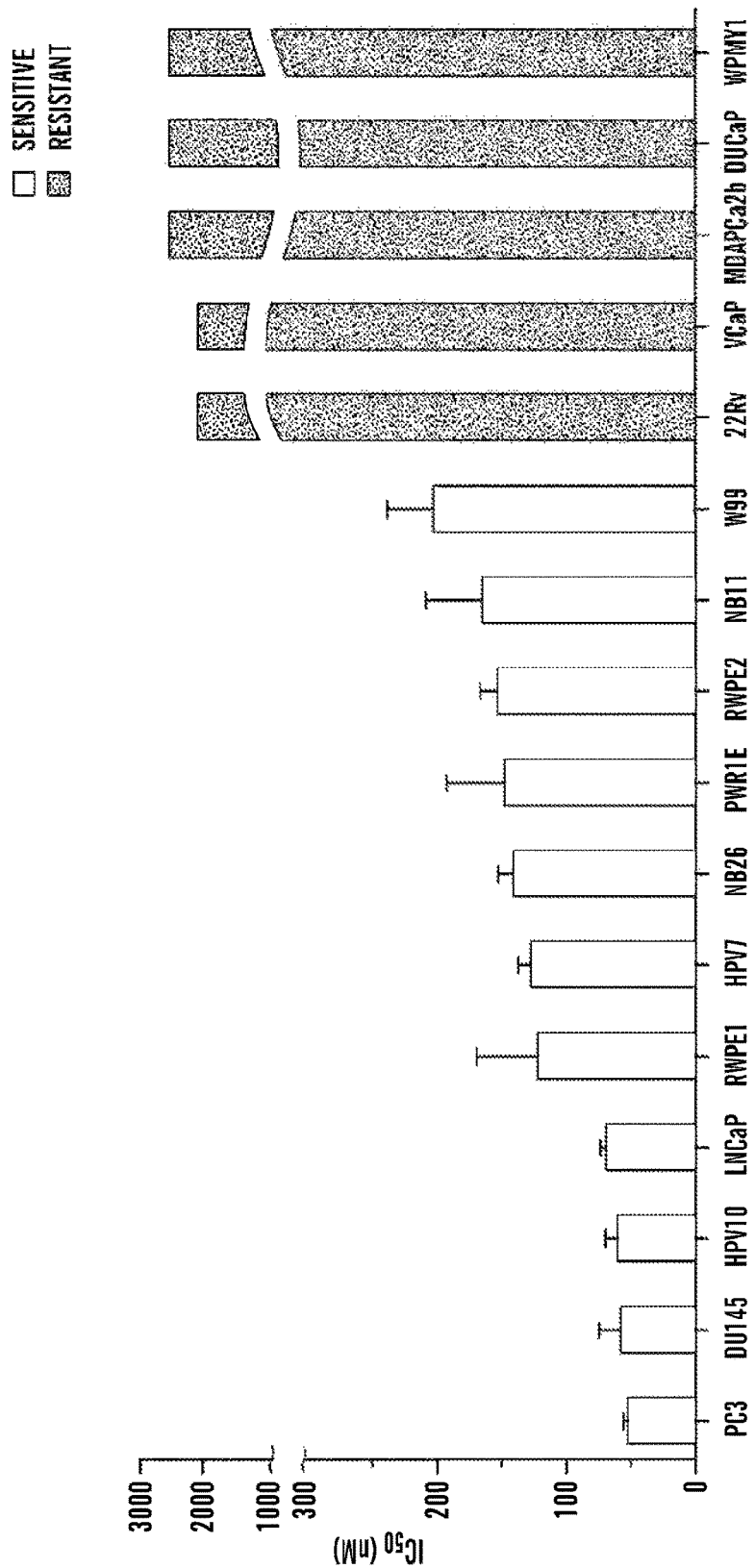
FIG. 9 shows the $IC_{50}$ values for 16 prostate cancer cell lines with variable sensitivity to dasatinib. Of the 16, 11 are sensitive and 5 are resistant to dasatinib.
Figure 10:
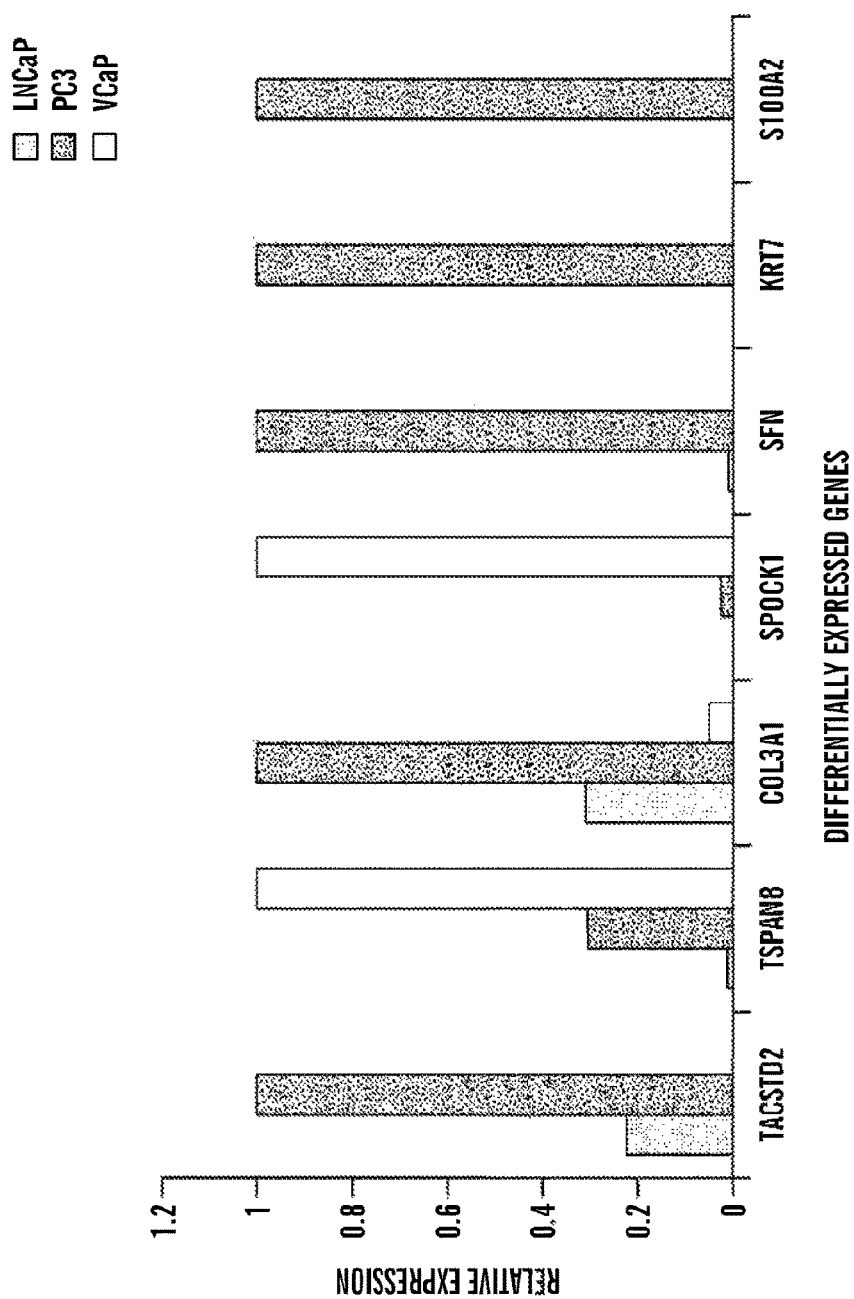
FIG. 10 shows the dasatinib sensitivity gene expression (relative expression) profile of prostate cancer cell lines, LNCaP, PC3 and VCaP for each of the seven genes.
Figure 11:
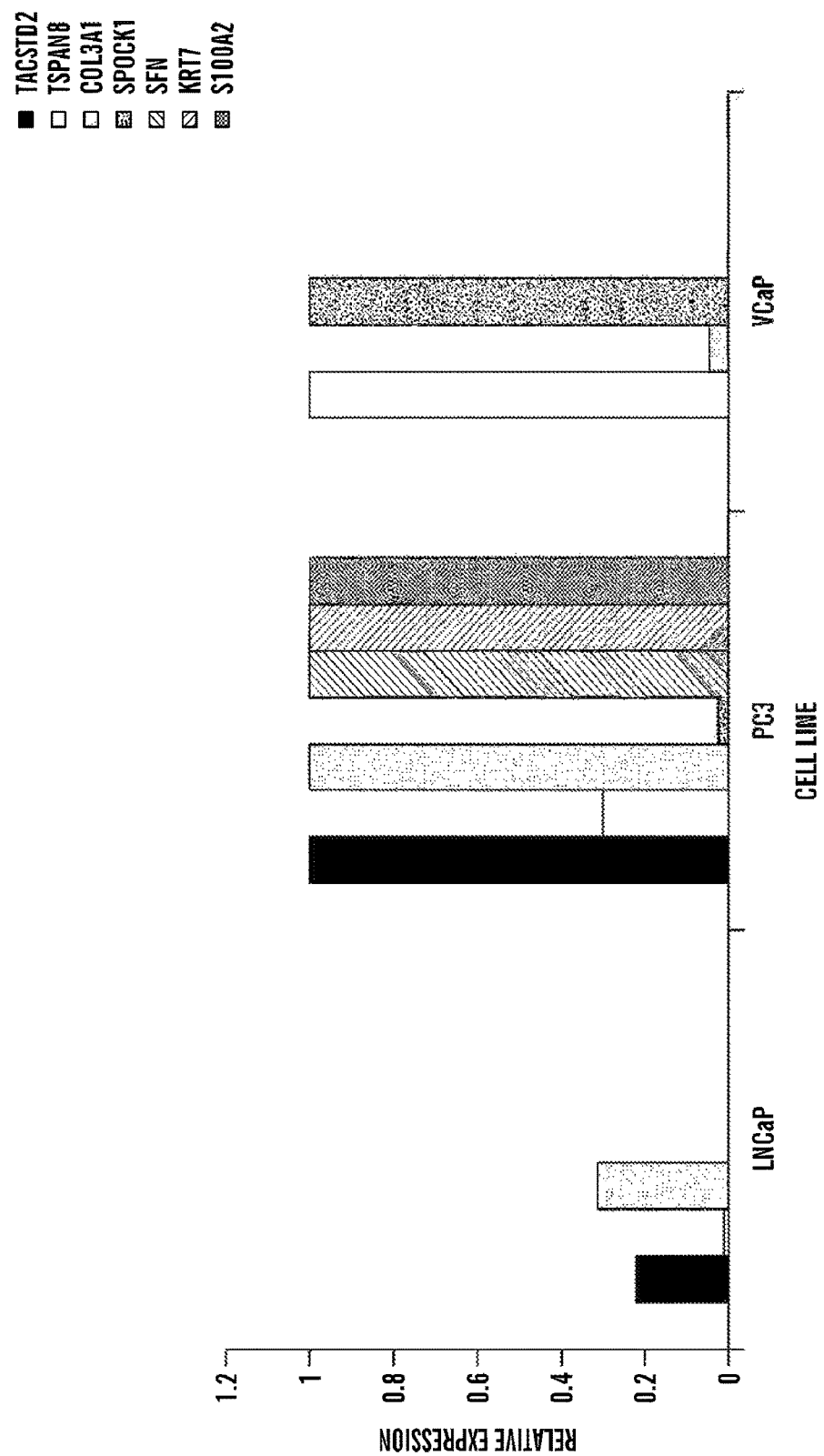
FIG. 11 shows the dasatinib sensitivity gene expression of prostate cancer cell lines, LNCaP, PC3 and VCaP, by cell line.

If we plot the separation of sensitive vs. resistant cell lines, excluding CWR, LAPC4, and LNCAP (2012), as they either lack an expected IC-50 dasatinib sensitivity profile or a definitive score, we obtain the boxplot in FIG. 6.

Next, we decided to rescale our sensitivity score equation so the results become easily interpretable, on a 0 to 100 range. The scores above were taken and the smallest score was subtracted from each score, and then divided by the difference between the largest and smallest scores. Finally, the values are multiplied by 100 to obtain a score that ranges from 0 to 100 (Eqn. 3). The process is elucidated in Table 9.

TABLE 9

| Sensitivity Score Rescaling to a 0-1 Score | | | | | | | | | |
|---|---|---|---|---|---|---|---|---|---|
| Scores | 1487 | 3000 | −1835 | 182.0 | 1620. | 946.6 | 579.9 | 2546 | 3103 |
| Scores − Min Score (−1835) | 3322 | 4835 | 0.000 | 2017 | 3455 | 2782 | 2415 | 4381 | 4938 |
| [Scores −Min Score (−1835)] Max Score (3103) − Min Score (−1835) | 0.673 | 0.979 | 0.00 | 0.408 | 0.700 | 0.563 | 0.489 | 0.887 | 1.00 |

Equation 3 gives the final rescaled sensitivity score for RT-PCR cycle threshold ($C_T$) data.

$$SCORE_{CT} = 100000 \times \left[\left(0.00657 \times \log_2\left(\frac{2^{-COL3A1_{CT}}}{2^{-GAPDH_{CT}}}\right)\right) - \right.$$

$$\left(0.127 \times \log_2\left(\frac{2^{-KRT7_{CT}}}{2^{-GAPDH_{CT}}}\right)\right) -$$

$$\left(0.00246 \times \log_2\left(\frac{2^{-SFN_{CT}}}{2^{-GAPDH_{CT}}}\right)\right) -$$

$$\left(0.206 \times \log_2\left(\frac{2^{-S100A2_{CT}}}{2^{-GAPDH_{CT}}}\right)\right) +$$

$$\left(0.000893 \times \log_2\left(\frac{2^{-SPOCK1_{CT}}}{2^{-GAPDH_{CT}}}\right)\right) -$$

$$\left(0.0838 \times \log_2\left(\frac{2^{-TACSTD2_{CT}}}{2^{-GAPDH_{CT}}}\right)\right) +$$

$$\left.\left(0.525 \times \log_2\left(\frac{2^{-TSPAN8_{CT}}}{2^{-GAPDH_{CT}}}\right)\right) - 1835\right] \div 4938 \quad \text{Equation 3}$$

In order to determine a tentative boundary that separates the dasatinib-resistant and sensitive cell lines using this score formula, the mean of the highest score of expected sensitivity (PC3 2012, 946.6) and the lowest score of expected resistance (22RV1 2012, 1487) was taken, then the same 100*(mean−1835)/4938 operation applied the formula was applied to obtain a score of 61.8 that separates the cell lines. In other words, using Eqn. 3, a score of <60 indicates sensitivity, while a score of >60 implies resistance.

| SENSITIVE | | | | | | RESISTANT | | | |
|---|---|---|---|---|---|---|---|---|---|
| 0 | 10 | 20 | 30 | 40 | 50 | 60 | 70 | 80 | 90 | 100 |

Using our predictive RT-PCR score (Eqn. 3), we calculated the predicted sensitivities of 7 cell lines (2011 and 2012 combined CT data for LNCaP, PC3, and VCaP). The results are shown in Table 10.

TABLE 10

| Detector | Score | Result | Expected Profile (IC-50) |
|---|---|---|---|
| 22RV1 | 67.29 | Resistant | Resistant |
| CWR | 97.91 | Resistant | — |
| LAPC4 | 0 | Sensitive | — |
| LNCAP | 25.62 | Sensitive | Sensitive |
| PC3 | 55.37 | Sensitive | Sensitive |
| VCAP | 83.94 | Resistant | Resistant |
| MDA | 69.97 | Resistant | Resistant |

Using the sensitivity score formula for RT-PCR CT values, the scores above were calculated. A score <60 indicates a sensitive profile and a score >60 indicates a resistant profile. The results for sensitivity are compared with the expected IC-50 dasatinib sensitivity result reported by Wang et al. Using our sensitivity score, we obtain 100% sensitivity across the 5 cell lines, unsurprisingly, as the score was derived using these cell lines.

CTC Isolation

Isolation of CTCs from CRPC patients is feasible and provides material that allows analysis at the DNA, RNA and protein level with sufficient quality and reproducibility to permit clinical decision making[40]. CTC number, as a continuous variable, is a strong independent predictor of survival with no threshold effect, and can be used as a marker for prognostification and real-time monitoring of response to treatment[41]. In a survival analysis of prostate cancer patients, PSA, lactate dehydrogenase, hemoglobin, and CTC were prognostic by univariate analysis, but only log CTC and log LDH provided independent prognostic information on survival time. This finding was consistent at baseline, and at four, eight, and twelve weeks post-therapy[42].

Changes in CTC count with treatment have also been suggested to be superior to PSA as a measure of clinical outcome. In an independent prostate cancer trial (IMMC38), post-treatment CTC number was more predictive of inferior survival than a 50% decline in PSA (ROC AUC 0.87 vs. 0.62, respectively)[43].

Recent advances in real-time molecular characterization of cancer cells allow us to profile CTCs captured with the use of magnetic bead-conjugated antibodies against epithelial-cell adhesion molecule (EpCAM). A CTC count ~20 (by flow cytometry) is adequate for molecular analysis of CTCs with qRT-PCR. The gene expression signature derived above is applied to CTC captured from CRPC patients.

CTC may be obtained from phlebotomy samples in a routine clinical practice setting. Various methods for the isolation and enrichment of circulating tumor cells are known in the art, including separation by size or density In one embodiment of the present invention, CTCs are obtained using flow cytometric techniques.

Figure 15:
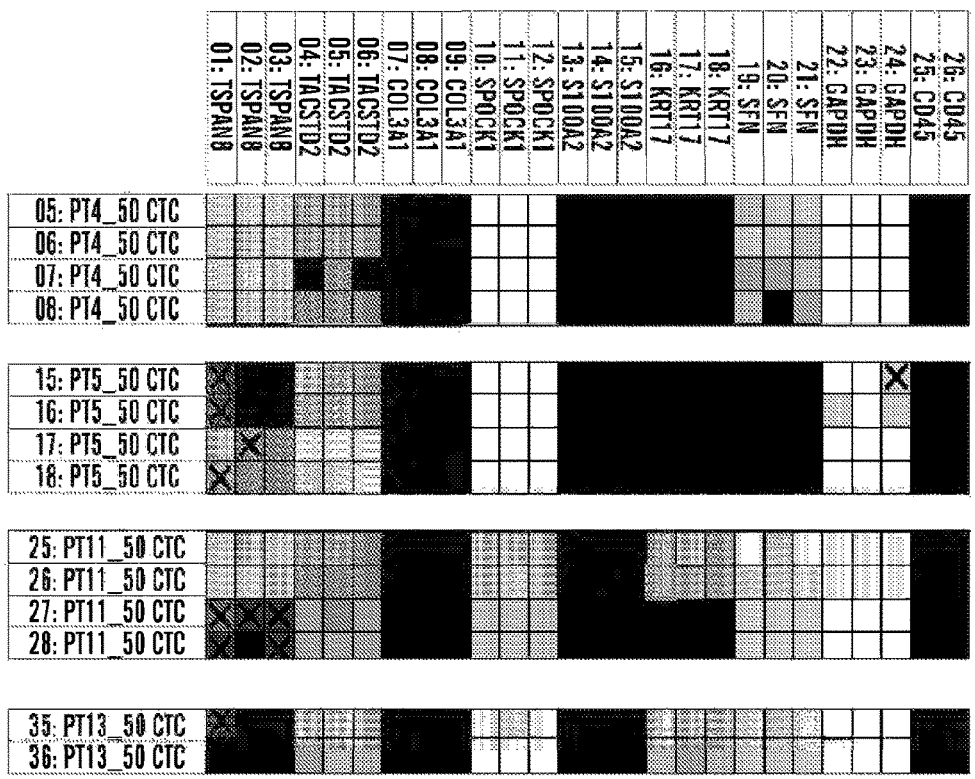
FIG. 15 shows the results of dasatinib signature gene panel scoring in CTC from patients with CRPC. The RT-PCR score and dasatinib signature prediction are shown for four patients (right panel).

Briefly, a blood sample is obtained from the patient and FICOLL extraction of peripheral blood mononuclear cells (PMBCs) is performed, to obtain the fraction containing CTCs. The cells of the harvested buffy coat then undergo cell sorting by FACS and an enriched population of EpCAM$^+$ CD45$^-$ DAPI$^-$ cells is obtained. Using flow cytometry, the detection rate and the absolute number of CTCs are increased and the purity of the cell isolation is improved. As shown in FIG. 15, CTC enrichment by flow cytometry captures more cells in and a more purified population compared to another commonly used method.

Patient Results

The dasatinib signature gene panel was used to score CTC from patients with CRPC. A correction for contaminating white blood cells in the CTC preparation was made using the following formula.

WBC correction:

$$Exp_{Corrected} = Exp_{CTC} - \frac{CD45_{CTC}}{CD45_{WBC}}(Exp_{WBC})$$

Figure 13:
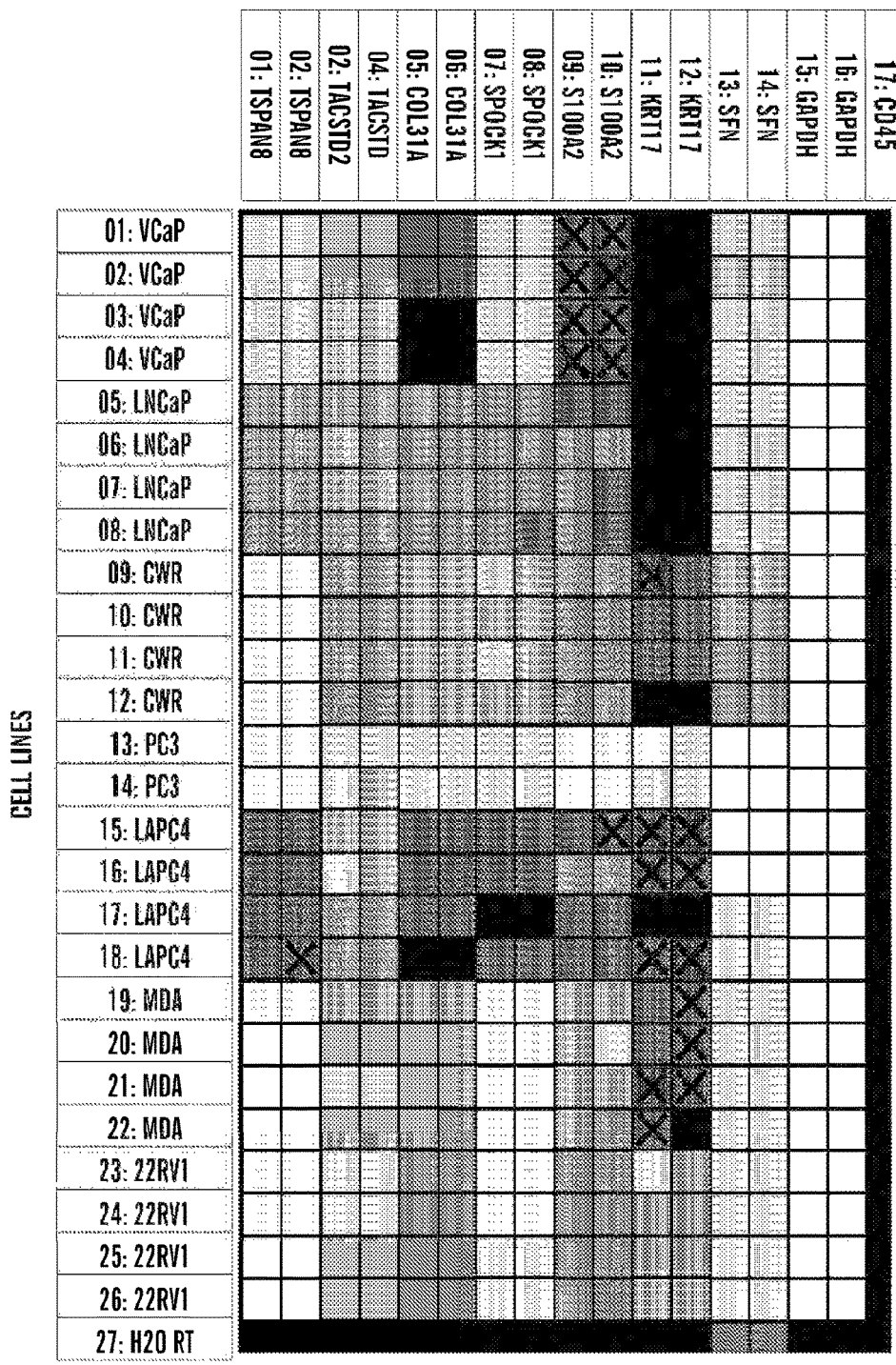
FIG. 13 shows that the dasatinib signature gene panel scoring differentiates sensitive vs. resistant cell lines correctly. Expression profile (Affy score) and RT-PCR (Fluidigm score) are shown for five cell lines (right panel).
Figure 14:
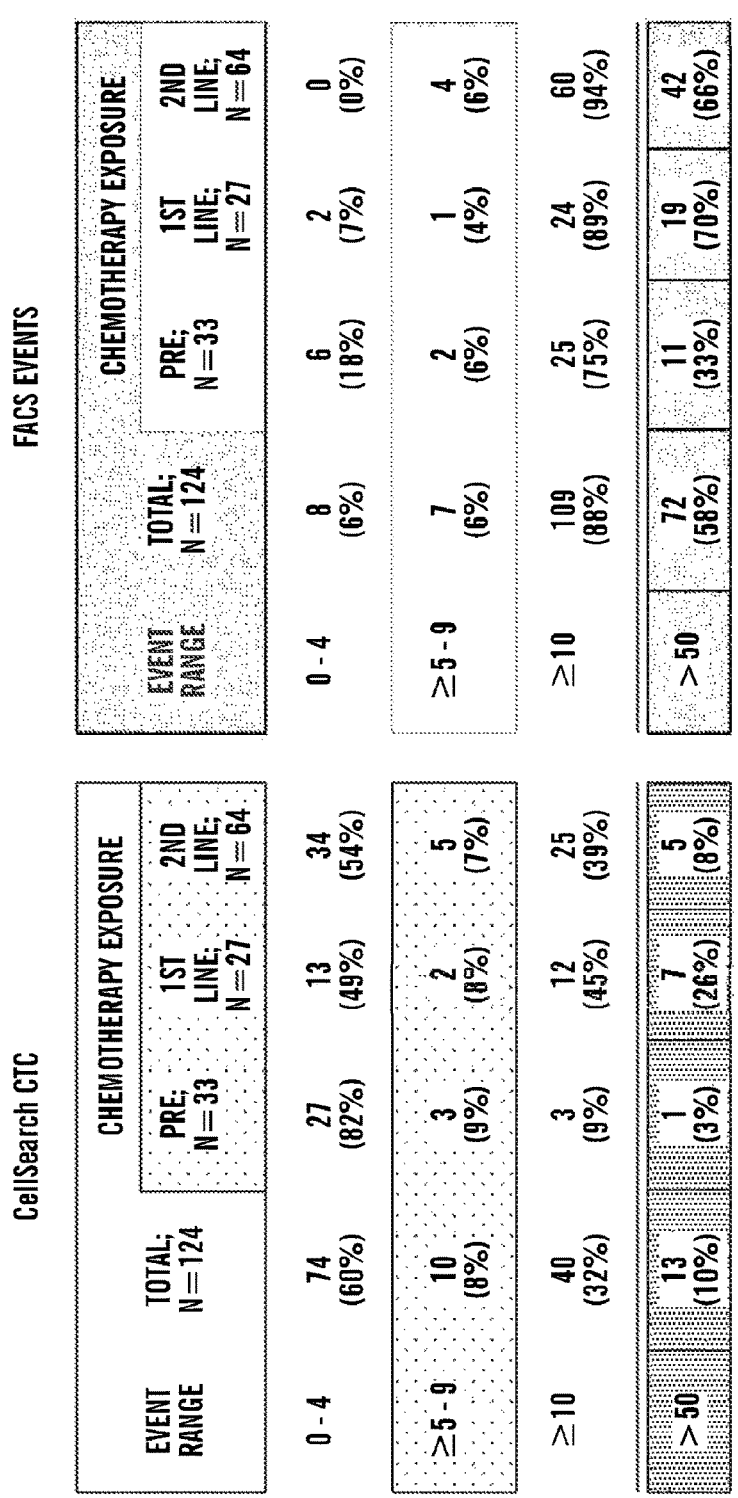
FIG. 14 is a comparison of flow cytometric CTC enrichment and CTC isolation by another commonly used method, CellSearch (Janssen Diagnostics, Raritan N.J.).

Of the 39 patients, 18 were indicated to have sensitivity to dasatinib treatment. The results for a few patients is shown in FIG. 13.

In summary, the present invention is based on the observation that the expression of a panel of 7 genes by circulating tumor cells can predict sensitivity/responsiveness of CRPC patients to treatment with dasatinib.

The panel of 7 genes was selected previously. qPCR measurements of these 7 genes were done on three cell-lines, LnCAP, PC3 and VCAP. The PC3 cell-line is dasatinib-sensitive, and LnCap and VCAP cell lines are dasatinib-resistant. To learn the combination of the 7 genes that best predicts sensitivity/resistance a logistic regression was run on the cell line dataset. A generalized linear model (glm) function from R statistical language was used.

The learning error is 0. The leave-one-out cross-validation error is 3%. The samples were then divided into training and test sets. The training set, used to learn the model, contains ⅔ of the samples (21 samples), and the learned model is then applied to the test dataset, which has ⅓ of samples (7 samples) making predictions. This procedure was performed 100 times, with samples randomly assigned to the training or test datasets, and the mean prediction error evaluated on the test sets is 10%.

The logistic model constructs the probability of a sample (cell-line/patient) being resistant in the following form:

$$p = (\exp(b0+bb))/(\exp(1+b0+bb)),$$

where bb=b1*TSPAN8+b2*TACSTD2+b3*COL3A1+b4*SPOCK1+b5*S100A2+b6*KRT7+b7*SFN

The b_i, i=1 . . . 7 parameters of the logistic model are fitted to the qPCR data from 28 cell-lines.

Figure 16:
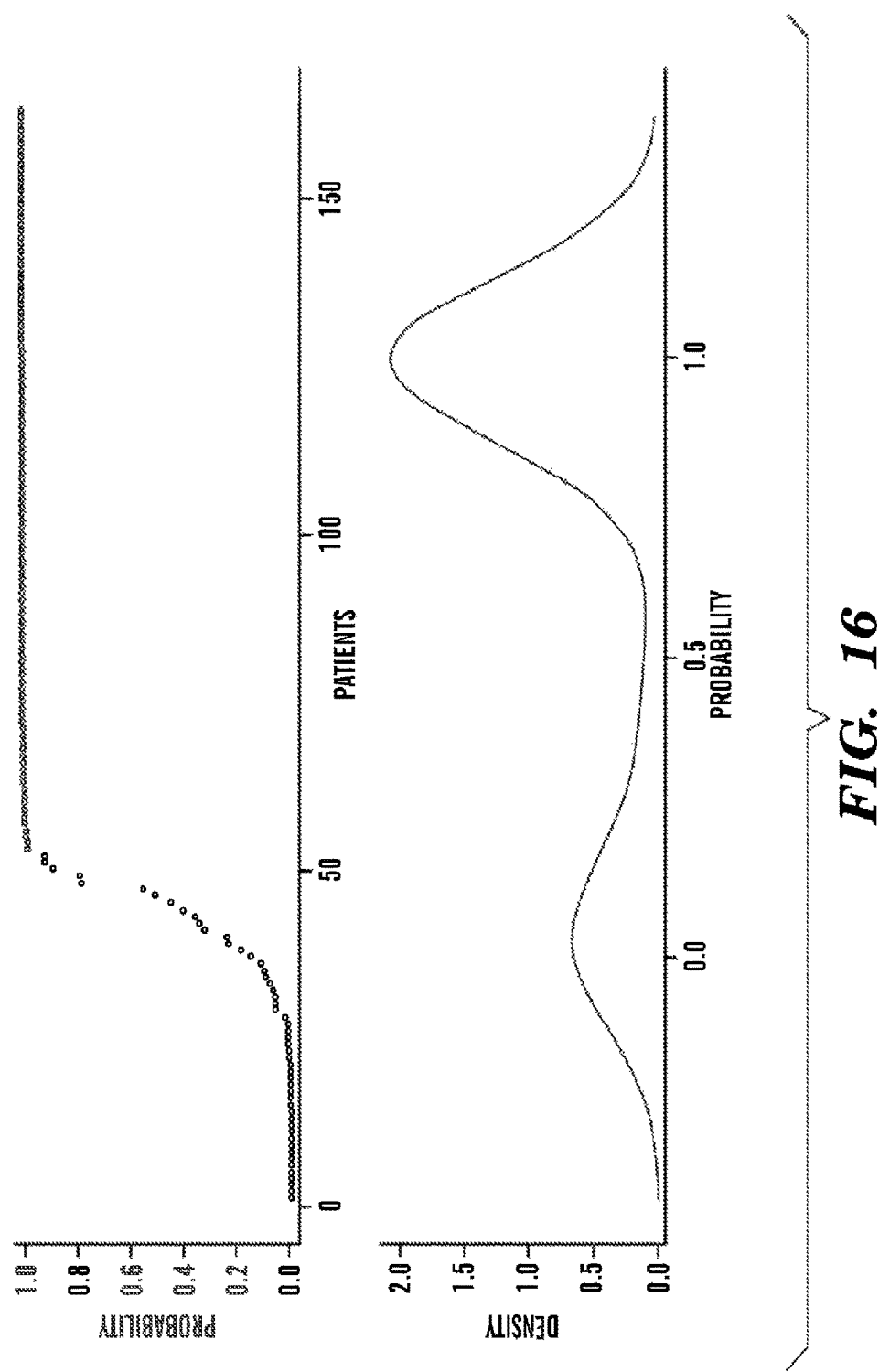
FIG. 16 shows the predicted probability of a patient's resistance to dasatinib treatment. Out of 163 patients, 24% (40 patients) are predicted to be sensitive (that is, the probability of being resistant is <0.2).

The constructed model is now applied to patient data to make predictions. Out of 163 patients, 24% (40 patients) are predicted to be sensitive (that is, the probability of being resistant is <0.2). (FIG. 16)

REFERENCES

1. Ohmachi, T. et al. Clinical significance of TROP2 expression in colorectal cancer. *Clinical cancer research: an official journal of the American Association for Cancer Research* 12, 3057-63 (2006).
2. Alberti, S., Miotti, S., Stella, M. & Klein, C. Biochemical characterization of Trop-2, a cell surface molecule expressed by human carcinomas: formal proof that the monoclonal antibodies T16 and MOv-16 recognize Trop-2. *Hybridoma* 11, 539-545 (1992).
3. Miotti, S. et al. Characterization of human ovarian carcinoma-associated antigens defined by novel monoclonal antibodies with tumor-restricted specificity. *International journal of cancer. Journal international du cancer* 39, 297-303 (1987).
4. Fradet, Y. et al. Cell surface antigens of human bladder cancer defined by mouse monoclonal antibodies. *Proceedings of the National Academy of Sciences of the United States of America* 81, 224-8 (1984).
5. Lipinski, M., Parks, D. R., Rouse, R. V. & Herzenberg, L. a Human trophoblast cell-surface antigens defined by monoclonal antibodies. *Proceedings of the National Academy of Sciences of the United States of America* 78, 5147-50 (1981).
6. Bignotti, E. et al. Trop-2 overexpression as an independent marker for poor overall survival in ovarian carcinoma patients. *European journal of cancer (Oxford, England: 1990)* 46, 944-53 (2010).
7. Cubas, R., Li, M., Chen, C. & Yao, Q. Trop2: a possible therapeutic target for late stage epithelial carcinomas. *Biochimica et biophysica acta* 1796, 309-14 (2009).
8. Guerra, E. et al. The Trop-2 signalling network in cancer growth. *Oncogene* 1-7 (2012).doi:10.1038/onc.2012.151
9. Trerotola, M. et al. Upregulation of Trop-2 quantitatively stimulates human cancer growth. *Oncogene* 1-12 (2012).doi:10.1038/onc.2012.36
10. Lin, H.-Y. et al. Activation of silenced tumor suppressor genes in prostate cancer cells by a novel energy restriction-mimetic agent. *The Prostate* (2012).doi:10.1002/pros.22530
11. Ibragimova, I. et al. Global reactivation of epigenetically silenced genes in prostate cancer. *Cancer prevention research (Philadelphia, Pa.)* 3, 1084-92 (2010).
12. Zöller, M. Tetraspanins: push and pull in suppressing and promoting metastasis. *Nature reviews. Cancer* 9, 40-55 (2009).
13. Nazarenko, I. et al. Cell surface tetraspanin Tspan8 contributes to molecular pathways of exosome-induced endothelial cell activation. *Cancer research* 70, 1668-78 (2010).
14. Richardson, M. M., Jennings, L. K. & Zhang, X. a Tetraspanins and tumor progression. *Clinical & experimental metastasis* 28, 261-70 (2011).
15. Wlazlinski, A., Engers, R. & Hoffmann, M. Downregulation of several fibulin genes in prostate cancer. *Prostate* 1780, 1770-1780 (2007).
16. Schulz, W. a et al. Changes in cortical cytoskeletal and extracellular matrix gene expression in prostate cancer are related to oncogenic ERG deregulation. *BMC Cancer* 10, 505 (2010).
17. Hermeking, H. The 14-3-3 cancer connection. *Nature reviews. Cancer* 3, 931-43 (2003).
18. Fu, H., Subramanian, R. R. & Masters, S. C. 14-3-3 Proteins: Structure, Function, and Regulation. *Annual review of pharmacology and toxicology* 40, 617-47 (2000).
19. van Hemert, M. J., Steensma, H. Y. & van Heusden, G. P. 14-3-3 Proteins: Key Regulators of Cell Division, Signalling and Apoptosis. *BioEssays: news and reviews in molecular, cellular and developmental biology* 23, 936-46 (2001).
20. Cheng, L. Loss of 14-3-3 in Prostate Cancer and Its Precursors. *Clinical Cancer Research* 10, 3064-3068 (2004).
21. Umbricht, C., Evron, E., Gabrielson, E. & Ferguson, A. Hypermethylation of 14-3-3 sigma (stratifin) is an early event in breast cancer. *Oncogene* 20, 3348-3353 (2001).
22. Donato, R. Functional roles of S100 proteins, calcium-binding proteins of the EF-hand type. *Biochimica et biophysics acta* 1450, 191-231 (1999).
23. Lee, S. W., Tomasetto, C., Swisshelm, K., Keyomarsi, K. & Sager, R. Down-regulation of a member of the S100 gene family in mammary carcinoma cells and reexpression by azadeoxycytidine treatment. *Proceedings of the National Academy of Sciences of the United States of America* 89, 2504-8 (1992).
24. Lee, S. W., Tomasetto, C. & Sager, R. Positive selection of candidate tumor-suppressor genes by subtractive hybridization. *Proceedings of the National Academy of Sciences of the United States of America* 88, 2825-9 (1991).

25. Wicki, R., Franz, C., Scholl, F. a, Heizmann, C. W. & Schäfer, B. W. Repression of the candidate tumor suppressor gene S100A2 in breast cancer is mediated by site-specific hypermethylation. *Cell calcium* 22, 243-54 (1997).
26. Nagy, N., Brenner, C. & Markadieu, N. S100A2, a Putative Tumor Suppressor Gene, Regulates In Vitro Squamous Cell Carcinoma Migration. *Laboratory Investigation* 81, 599-612 (2001).
27. Mertz, K. D. et al. Association of cytokeratin 7 and 19 expression with genomic stability and favorable prognosis in clear cell renal cell cancer. *International journal of cancer. Journal international du cancer* 123, 569-76 (2008).
28. Liu, X., Wu, H., Byrne, M. & Krane, S. Type III collagen is crucial for collagen I fibrillogenesis and for normal cardiovascular development. *Proceedings of the* 94, 1852-1856 (1997).
29. Stanbrough, M. et al. Increased expression of genes converting adrenal androgens to testosterone in androgen-independent prostate cancer. *Cancer research* 66, 2815-25 (2006).
30. Wang, X.-D. et al. Identification of candidate predictive and surrogate molecular markers for dasatinib in prostate cancer: rationale for patient selection and efficacy monitoring. *Genome biology* 8, R255 (2007).
31. Thellin, O. et al. Housekeeping genes as internal standards: use and limits. *Journal of biotechnology* 75, 291-5 (1999).

We claim:

1. A method of selecting treatment with dasatinib for a prostate cancer patient comprising:
    (a) contacting RNA from a circulating tumor cell (CTC) obtained from the patient with a primer set for measuring expression of gene products of genes TACSTD2, SPAN8, COL3A 1, SPOCK1, SFN, KRT7, and S100A2, the set comprising a plurality of synthetic oligonucleotide primers, each of which is capable of hybridizing to an expression product of one of said genes such that the plurality of primers can detect the gene products of all of said genes to measure the relative expression of each of said genes in the CTC from the patient;
    (b) contacting RNA from a known dasatinib-sensitive cell with a primer set for measuring expression of gene products of genes TACSTD2, TSPAN8, COL3A1, SPOCK1, SFN, KRT7, and S100A2, the set comprising a plurality of synthetic oligonucleotide primers, each of which is capable of hybridizing to an expression product of one of said genes such that the plurality of primers can detect the gene products of all of said genes to measure the relative expression of each of said genes in said known dasatinib-sensitive cell;
    (c) comparing the expression level of said genes in the CTC from the patient with the expression level of said genes in a known dasatinib-sensitive cell;
    (d) treating the patient with dasatinib when the expression level of the genes in the CTC is equal to or less than the expression level of the genes in a known dasatinib-sensitive cell.

2. A method of selecting dasatinib treatment for a prostate cancer patient, the method comprising:
    (a) contacting RNA from a CTC obtained from the patient with a primer set for measuring expression of gene products of genes TACSTD2, TSPAN8, COL3A1, SPOCK1, SFN, KRT7 and S100A2, the set comprising a plurality of synthetic oligonucleotide primers, each of which is capable of hybridizing to an expression product of one of said genes such that the plurality of primers can detect the gene products of all of said genes to measure the relative expression of each of said genes in said CTC;
    (b) assigning a score between 0 and 100 to said expression value using the formula $$SCORE_{CT} = 100000 \times \left[ \left( 0.00657 \times \log_2\left(\frac{2^{-COL3A1_{CT}}}{2^{-GAPDH_{CT}}}\right) \right) - \left( 0.127 \times \log_2\left(\frac{2^{-KRT7_{CT}}}{2^{-GAPDH_{CT}}}\right) \right) - \left( 0.00246 \times \log_2\left(\frac{2^{-SFN_{CT}}}{2^{-GAPDH_{CT}}}\right) \right) - \left( 0.206 \times \log_2\left(\frac{2^{-S100A2_{CT}}}{2^{-GAPDH_{CT}}}\right) \right) + \left( 0.000893 \times \log_2\left(\frac{2^{-SPOCK1_{CT}}}{2^{-GAPDH_{CT}}}\right) \right) - \left( 0.0838 \times \log_2\left(\frac{2^{-TACSTD2_{CT}}}{2^{-GAPDH_{CT}}}\right) \right) + \left( 0.525 \times \log_2\left(\frac{2^{-TSPAN8_{CT}}}{2^{-GAPDH_{CT}}}\right) \right) - 1835 \right] \div 4938$$

wherein a score ≤60 indicates a dasatinib sensitive profile and a score >60 indicates a resistant profile;
    (c) treating the patient with dasatinib when the score is <60.

3. A method for selecting dasatinib treatment for a prostate cancer patient comprising:
    (a) contacting RNA from a CTC obtained from the patient with a primer set for measuring expression of gene products of genes TACSTD2, TSPAN8, COL3A1, SPOCK1, SFN, KRT7, and S100A2, the set consisting of a plurality of synthetic oligonucleotide primers, each of which is capable of hybridizing to an expression product of one of said genes such that the plurality of primers can detect the gene products of every one of said genes to measure the relative expression of each of said genes in the CTC;
    (b) calculating a sensitivity score for each cell using one of formulas:

$$SCORE_{Affy} = (0.114 * TACSTD2_{Affy}) - (0.703 * TSPAN8_{Affy}) - (0.036 * COL3A1_{Affy}) - (0.002 * SPOCK1_{Affy}) + (0.022 * SFN_{Affy}) + (0.514 * KRT7_{Affy}) + (0.518 * S100A2_{Affy}) \qquad \text{Eqn. 1}$$

$$SCORE_{CT} = 1000 * \left[ \left( 0.00657 \times \log_2\left(\frac{2^{-COL3A1_{CT}}}{2^{-GAPDH_{CT}}}\right) \right) - \left( 0.127 \times \log_2\left(\frac{2^{-KRT7_{CT}}}{2^{-GAPDH_{CT}}}\right) \right) - \left( 0.00246 \times \log_2\left(\frac{2^{-SFN_{CT}}}{2^{-GAPDH_{CT}}}\right) \right) - \left( 0.206 \times \log_2\left(\frac{2^{-S100A2_{CT}}}{2^{-GAPDH_{CT}}}\right) \right) + \left( 0.000893 \times \log_2\left(\frac{2^{-SPOCK1_{CT}}}{2^{-GAPDH_{CT}}}\right) \right) - \left( 0.0838 \times \log_2\left(\frac{2^{-TACSTD2_{CT}}}{2^{-GAPDH_{CT}}}\right) \right) + \left( 0.525 \times \log_2\left(\frac{2^{-TSPAN8_{CT}}}{2^{-GAPDH_{CT}}}\right) \right) \right] \qquad \text{Eqn. 2}$$

or $$SCORE_{CT} = 100000 \times \left[ \left( 0.00657 \times \log_2\left(\frac{2^{-COL3A1_{CT}}}{2^{-GAPDH_{CT}}}\right) \right) - \qquad \text{Eqn. 3}$$

$$\left(0.127 \times \log_2\left(\frac{2^{-KRT7_{CT}}}{2^{-GAPDH_{CT}}}\right)\right) -$$

$$\left(0.00246 \times \log_2\left(\frac{2^{-SFN_{CT}}}{2^{-GAPDH_{CT}}}\right)\right) -$$

$$\left(0.206 \times \log_2\left(\frac{2^{-S100A2_{CT}}}{2^{-GAPDH_{CT}}}\right)\right) +$$

$$\left(0.000893 \times \log_2\left(\frac{2^{-SPOCK1_{CT}}}{2^{-GAPDH_{CT}}}\right)\right) -$$

$$\left(0.0838 \times \log_2\left(\frac{2^{-TACSTD2_{CT}}}{2^{-GAPDH_{CT}}}\right)\right) +$$

$$\left(0.525 \times \log_2\left(\frac{2^{-TSPAN8_{CT}}}{2^{-GAPDH_{CT}}}\right)\right) - 1835\right] \div 4938;$$

and (c) comparing the sensitivity score for the CTC with the sensitivity score for a known dasatinib-sensitive cell;

(d) treating the patient with dasatinib when the sensitivity score for the CTC is equal to or less than the sensitivity score for the known dasatinib-sensitive cell.

4. The method of claim 2, wherein said relative expression of gene products is determined using polymerase chase reaction (PCR).

5. The method of claim 4, wherein the PCR platform is a microfluidic RT-PCR platform.

6. The method of claim 2, wherein said circulating tumor cell is EpCAM$^+$ CD45$^-$ DAPI$^-$.

7. The method of claim 2, where said circulating tumor cell is isolated using flow cytometry.

8. The method of claim 3, wherein the sensitivity score is calculated using Eqn. 1 and microarray data as input.

9. The method of claim 3, wherein the sensitivity score is calculated using Eqn. 2 or Eqn. 3 and RT-PCR expression data as input.

10. The method of claim 2, wherein said gene product is RNA or cDNA.

11. The method of claim 3, wherein said expression product is RNA or cDNA.

* * * * *